US012559499B2

(12) United States Patent
Hurley et al.

(10) Patent No.: US 12,559,499 B2
(45) **Date of Patent: *Feb. 24, 2026**

(54) USES OF COMPOUNDS HAVING ANTI-HSV-1 ACTIVITY

(71) Applicants: Arizona Board of Regents on Behalf of the University of Arizona, Tucson, AZ (US); Università degli Studi di Padova, Padua (IT)

(72) Inventors: Laurence Hurley, Tucson, AZ (US); Sara Richter, Padua (IT); Paola Soldà, Padua (IT)

(73) Assignees: Arizona Board of Regents on Behalf of the University of Arizona, Tucson, AZ (US); Universitá degli Studi di Padova, Padua (IT)

(*) Notice: Subject to any disclaimer, the term of this patent is extended or adjusted under 35 U.S.C. 154(b) by 952 days.

This patent is subject to a terminal disclaimer.

(21) Appl. No.: 17/426,935

(22) PCT Filed: Jan. 29, 2020

(86) PCT No.: PCT/US2020/015716

§ 371 (c)(1),
(2) Date: Jul. 29, 2021

(87) PCT Pub. No.: WO2020/160174

PCT Pub. Date: Aug. 6, 2020

(65) Prior Publication Data

US 2022/0105083 A1 Apr. 7, 2022

Related U.S. Application Data

(60) Provisional application No. 62/798,293, filed on Jan. 29, 2019.

(51) Int. Cl.

| | |
|---|---|
| ***C07D 487/14*** | (2006.01) |
| ***A61K 31/4709*** | (2006.01) |
| ***A61K 31/4738*** | (2006.01) |
| ***A61K 45/06*** | (2006.01) |
| ***A61P 35/00*** | (2006.01) |
| *A61K 31/47* | (2006.01) |

(52) U.S. Cl.

CPC ........ *C07D 487/14* (2013.01); *A61K 31/4709* (2013.01); *A61K 31/4738* (2013.01); *A61K 45/06* (2013.01); *A61P 35/00* (2018.01); *A61K 31/47* (2013.01)

(58) Field of Classification Search

CPC ............................ C07D 487/00; C07D 487/14

See application file for complete search history.

(56) References Cited

U.S. PATENT DOCUMENTS

2007/0249564 A1 10/2007 Erion et al.
2017/0334905 A1 11/2017 Haddach

FOREIGN PATENT DOCUMENTS

WO WO 1996/010015 4/1996
WO WO 2015/034665 3/2015

OTHER PUBLICATIONS

Ahmed, et al. J. Pharm. Pharmaceut Sci. 15(1) 52-72, 2012.*
Wang, et al. J. Med. Chem. 2017, 60, 2840-2852.*
HIV/AIDS [online] retrieved from the internet on May 31, 2024; https://www.mayoclinic.org/diseases-conditions/hiv-aids/symptoms-causes/syc-20373524.*
Everything you need to know about oral and genital herpes [online] retrieved from the internet on May 31, 2024; https://www.healthline.com/health/herpes-simplex.*
Herpes simplex virus [online] retrieved from the internet on May 31, 2024; https://www.who.int/news-room/fact-sheets/detail/herpes-simplex-virus.*
Artusi et al., The Herpes Simplex Virus-1 genome contains multiple clusters of repeated G-quadruplex: Implications for the antiviral activity of a G-quadruplex ligand. Antiviral Res. Jun. 2015;118:123-31.
Bundgaard. Design of Prodrugs, Elsevier, 1985. TOC only. 2 pages.
Burger's Medicinal Chemistry and Drug Discovery, 5th Ed., M. Wolff (ed.), John Wiley & Sons, 1995, pp. 172-178.
Burger's Medicinal Chemistry and Drug Discovery, 5th Ed., M. Wolff (ed.), John Wiley & Sons, 1995, pp. 949-982.
Butovskaya et al. Major G-Quadruplex Form of HIV-1 LTR Reveals a (3 + 1) Folding Topology Containing a Stem-Loop. J Am Chem Soc. Oct. 24, 2018;140(42):13654-13662.
Callegaro et al., A core extended naphtalene diimide G-quadruplex ligand potently inhibits herpes simplex virus 1 replication. Sci Rep. May 24, 2017;7(1):2341. 1-9.
Daelemans et al., A time-of-drug addition approach to target identification of antiviral compounds. Nat Protoc. Jun. 2011;6(6):925-33.
Elion et al., Acyclovir: discovery, mechanism of action, and selectivity. J Med Virol. 1993; Suppl 1:2-6.
Higuchi et al., Pro-Drugs as Novel Delivery Systems. Am. Chem. Soc., 1975. TOC only. 14 pages.
International Search Report & Written Opinion, International Patent Application No. PCT/US20/15716, mailed May 20, 2020, 14 pages.
Ou et al., Stabilization of G-quadruplex DNA and down-regulation of oncogene c-myc by quindoline derivatives. J Med Chem. Apr. 5, 2007;50(7):1465-74.
Silverman. The Organic Chemistry of Drug Design and Drug Action, Academic Press, San Diego, CA. 1992. pp. 352-401.
Yuan et al., Mass spectrometry of G-quadruplex DNA: formation, recognition, property, conversion, and conformation. Mass Spectrom Rev. Nov.-Dec. 2011;30(6):1121-42.

* cited by examiner

*Primary Examiner* — Shawquia Jackson
(74) *Attorney, Agent, or Firm* — Casimir Jones, S.C.; Robert A. Goetz

(57) ABSTRACT

This invention provides methods of treating, suppressing, inhibiting, reducing an incidence, reducing the pathogenesis of, ameliorating the symptoms of, or ameliorating the secondary symptoms of a primary or recurring Herpes Simplex Virus (HSV) infection, or prolonging the latency to a relapse of an HSV infection, and disorders and symptoms associated with same in a subject comprising the step of contacting the subject with a composition comprising a quindoline (or similar) structure having significant anti-HSV activity.

13 Claims, 4 Drawing Sheets

B

USES OF COMPOUNDS HAVING ANTI-HSV-1 ACTIVITY

CROSS REFERENCE TO RELATED APPLICATIONS

This application is a U.S. 371 national phase entry of International Patent Application No. PCT/US2020/015716, filed Jan. 29, 2020, which claims priority to and the benefit of U.S. Provisional Application No. 62/798,293, filed Jan. 29, 2019, which are hereby incorporated by reference in their entireties.

STATEMENT REGARDING FEDERALLY SPONSORED RESEARCH OR DEVELOPMENT

This invention was made with government support under Grant No. P50 CA095060 awarded by National Institutes of Health. The government has certain rights in the invention.

FIELD OF THE INVENTION

This invention provides methods of treating, suppressing, inhibiting, reducing an incidence, reducing the pathogenesis of, ameliorating the symptoms of, or ameliorating the secondary symptoms of a primary or recurring Herpes Simplex Virus type 1 and 2 (HSV) infection, or prolonging the latency to a relapse of an HSV infection, and disorders and symptoms associated with same in a subject comprising the step of contacting the subject with a composition comprising a quindoline (or similar) structure having significant anti-HSV activity.

INTRODUCTION

Human infection with herpes simplex virus (HSV) is typically acquired through intimate contact and causes oral lesions. HSV usually causes oral ulcers and genital ulcers. A person infected with HSV will always be a carrier of the virus. After initial infection, lesions heal and HSV exists in a dormant, latent state in sensory neurons. Periodically, HSV reactivates from latently infected neurons and causes new ulcers to form at the skin and mucous membrane surface. Newborn infants and immunosuppressed individuals are particularly vulnerable to HSV infection, often having a disseminated infection with fatal results. Ocular HSV infection, a leading cause of blindness, is another serious consequence of the virus. Furthermore, genital HSV infection results in a two-fold increase in HIV transmission rate. Therefore, improved methods for treating and preventing HSV infection are urgently needed.

The present invention addresses this need.

SUMMARY OF THE INVENTION

Experiments conducted during the course of developing embodiments for the present invention demonstrated that specific small-molecules having a quindoline (or similar) structure described herein displayed significant anti-herpes simplex virus (anti-HSV) activity. In particular, it was shown that in displaying significant anti-HSV activity the compound GSA-0932

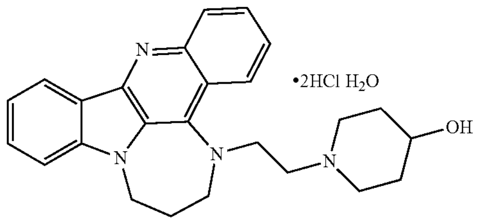

•2HCl $H_2O$

GSA0932

Chemical Formula: C25H28N4O 2HCl H2OC$_{25}$H$_{28}$N$_4$O ( Molecular Weight: 409.8241400.53 )

acted in early events of the viral life cycle, greatly stabilized the HSV G-quadruplex structures (G4s), and binded G4s with a preference for the HSV G4s vs the telomeric sequence.

As such, the present invention relates to use of a class of small-molecules having a quindoline (or similar) structure having significant anti-HSV activity. In particular, the present invention provides methods for inhibiting viral activity (e.g., HSV activity) and/or expression through stabilization of G-quadruplex structures related to viral activity and/or expression, and methods for treating any type of condition characterized with viral activity (e.g., HSV activity).

Indeed, the present invention provides methods of treating, suppressing, inhibiting, reducing an incidence, reducing the pathogenesis of, ameliorating the symptoms of, or ameliorating the secondary symptoms of a primary or recurring Herpes Simplex Virus (HSV) infection, or prolonging the latency to a relapse of an HSV infection, and disorders and symptoms associated with same in a subject comprising the step of contacting the subject with a composition comprising a small molecule having a quindoline (or similar) structure having significant anti-HSV activity.

Accordingly, the present invention contemplates that exposure of animals (e.g., humans) suffering from any type of condition characterized with activity related to unstable G-quadruplex structures to the compounds having a quindoline (or similar) structure will result in an effective treatment of such conditions outright and/or render such conditions more susceptible to additional therapies (e.g., anti-viral therapies).

For example, in some embodiments, the inhibition of viral activity and/or expression (e.g., HSV activity and/or expression) occurs through, for example, stabilization of G-quadruplex structures related to such viral activity and/or expression. The present invention contemplates that such viral antagonists satisfy an unmet need for the treatment of multiple viral conditions (e.g., conditions related to HSV activity and/or expression), either when administered as monotherapy, or when administered in a temporal relationship with additional agent(s), such as other anti-viral therapies.

The quindoline (or similar) compounds of the present invention may exist as stereoisomers including optical isomers. The invention includes all stereoisomers, both as pure individual stereoisomer preparations and enriched preparations of each, and both the racemic mixtures of such stereoisomers as well as the individual diastereomers and enantiomers that may be separated according to methods that are well known to those of skill in the art.

The compounds of the invention are useful for the treatment, amelioration, or prevention of any type of condition characterized with activity related to unstable G-quadruplex structures disorders (e.g., viral conditions (e.g., viral conditions related to HSV activity)).

In certain embodiments, the present invention provides methods/uses for the treatment, amelioration, or prevention of viral disorders (e.g., viral disorders related to HSV (e.g., HSV-1) (e.g., HSV-2) activity) through administration of specific quindoline (or similar) compounds. In certain embodiments, the compounds can be used to treat, ameliorate, or prevent a viral condition that is characterized by resistance to viral therapies. In certain embodiments, the viral condition is any type of viral condition characterized with unstable G-quadruplex activity.

In certain embodiments, the present invention provides methods of treating a Herpes Simplex Virus (HSV) infection in a subject comprising the steps of: (a) administering a therapeutically effective amount of a composition comprising a small molecule having a quindoline (or similar) structure having significant anti-HSV activity to said subject.

In certain embodiments, the present invention provides methods of suppressing a recurrent HSV infection in a subject comprising the steps of: (a) administering a therapeutically effective amount of a composition comprising a small molecule having a quindoline (or similar) structure having significant anti-HSV activity to said subject.

Such methods are not limited to particular viral disorder related to HSV or particular HSV infection types. In some embodiments, the HSV infection or viral disorder related to HSV include, but are not limited, to an oral infection (e.g., herpes) (e.g., oral ulcers), a genital infection (e.g., genital herpes), a neonatal infection, an ocular infection, and a central nervous system disorder (e.g., meningitis, encephalitis). In some embodiments, the viral disorder related to HSV or particular HSV infection type is a flare, a recurrence or a primary infection.

Such methods are not limited to particular manner of treating or suppressing the HSV infection. In some embodiments, treating the HSV infection comprises reducing the frequency of recurrent lesions. In some embodiments, treating the HSV infection comprises inducing rapid clearance of the HSV infection in the subject. In some embodiments, treating the HSV infection comprises reducing the severity of the HSV infection in the subject. In some embodiments, suppressing a recurrent HSV infection comprises preventing latent infection of HSV in the subject.

Such uses and methods are not limited to a particular manner of administration of the composition comprising a small molecule having a quindoline (or similar) structure having significant anti-HSV activity. In some embodiments, the composition is administered intramuscularly, epidermally, subcutaneously, intravaginally, or via intra-respiratory mucosal injection.

Such uses and methods and uses are not limited to specific quindoline compounds.

In some embodiments, the specific quindoline compounds encompassed within Formula I are utilized:

(Formula I)

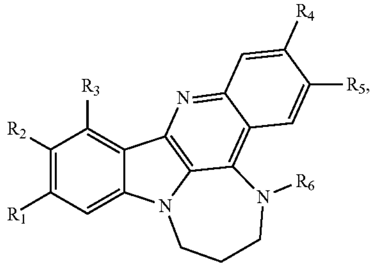

including pharmaceutically acceptable salts, solvates, and/or prodrugs thereof.

Formula I is not limited to a particular chemical moiety for R1, R2, R3, R4, R5 and R6. In some embodiments, the particular chemical moiety for R1, R2, R3, R4, R5 and R6 independently include any chemical moiety that permits the resulting compound to stabilize G-quadruplex structures.

In some embodiments, the particular chemical moiety for R1, R2, R3, R4, R5 and R6 independently include any chemical moiety that permits the resulting compound to inhibit HSV activity and/or expression. In some embodiments, the particular chemical moiety for R1, R2, R3, R4, R5 and R6 independently include any chemical moiety that permits the resulting compound to inhibit HSV activity and/or expression through stabilization of G-quadruplex structures related to HSV activity and/or expression.

In some embodiments, the specific quindoline compounds encompassed within Formula II are utilized:

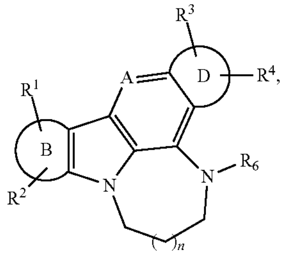

or a pharmaceutically acceptable salt thereof.

Formula II is not limited to a particular chemical structure. In some embodiments, the compound encompassed by Formula II is capable of stabilizing G-quadruplex structures.

In some embodiments, the compound encompassed by Formula II is capable of inhibiting HSV activity and/or expression. In some embodiments, the compound encompassed by Formula II is capable of inhibiting HSV activity and/or expression through stabilization of G-quadruplex structures related to HSV activity and/or expression.

In some embodiments, the compounds shown in Table I are utilized.

Any of the specific quindoline (or similar) compounds of the present invention may exist as stereoisomers including optical isomers. The invention includes all stereoisomers, both as pure individual stereoisomer preparations and enriched preparations of each, and both the racemic mixtures of such stereoisomers as well as the individual diastereomers and enantiomers that may be separated according to methods that are well known to those of skill in the art.

In some embodiments, such methods and uses utilize pharmaceutical compositions comprising such specific quindoline compounds in a pharmaceutically acceptable carrier.

In certain embodiments, the present invention provides methods for the prophylaxis or treatment of a viral disease characterized with unstable G-quadruplex activity, the method comprising administering a therapeutically effective amount of a composition comprising a quindoline (or similar) structure having significant anti-HSV activity to a subject in need of such treatment, wherein the disease or condition characterized by unstable G-quadruplex activity is a viral condition.

In some embodiments, the viral disease characterized with unstable G-quadruplex activity is selected from Adenovirus infections, Herpes virus infections, Papillomavirus infections, Parvovirus infections, Polyomavirus infections, Poxvirus infections, Arbovirus infection, Arenavirus infections, Astrovirus infections, Birnavirus infections, Bunyavirus infections, Calicivirus infections, Coronavirus infections, Flavivirus infections, Hantavirus infections, Hepatitis virus infections, including Hepatitis A, Hepatitis B, Hepatitis C, and Hepatitis D, Mononegavirus infections, including Filovirus infections, Paramyxovirus infections, and Rhabdovirus infections, Nidovirales Infections, Orthomyxoviridae infections including influenza virus infections, Picornavirus infections including Enterovirus infections, Reovirus infections including Rotavirus infections, Retrovirus infections including lentivirus infections, such as HIV infections, Togavirus infections including Rubivirus infections.

In some embodiments, the viral disease is an Adenovirus infection.

In some embodiments, the viral disease is selected from a Herpes virus infection and a Picoma virus infection.

In some embodiments, the herpes virus infection is caused by HSV-1, HSV-2 and/or varicella zoster virus.

In some embodiments, subject is a human subject.

DEFINITIONS

Figure 1:
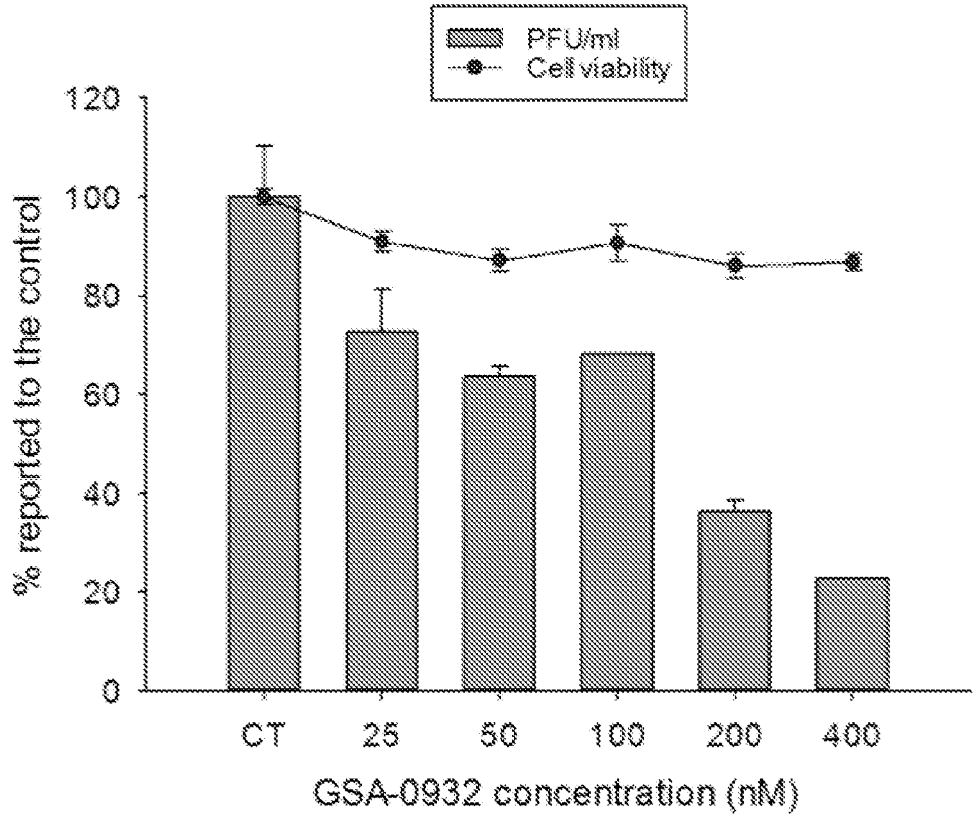
FIG. 1: Antiviral activity and cytotoxicity of GSA-0932. This figure is representative of the antiviral (grey bars) and cytotoxicity (black lane and dots) experiments performed with GSA-0932.

Terms used herein may be preceded and/or followed by a single dash, "—", or a double dash, "=", to indicate the bond order of the bond between the named substituent and its parent moiety; a single dash indicates a single bond and a double dash indicates a double bond. In the absence of a single or double dash it is understood that a single bond is formed between the substituent and its parent moiety; further, substituents are intended to be read "left to right" unless a dash indicates otherwise. For example, $C_1$-$C_6$alkoxycarbonyloxy and —OC(O)$C_1$-$C_6$alkyl indicate the same functionality; similarly arylalkyl and alkylaryl indicate the same functionality.

The term "alkenyl" as used herein, means a straight or branched chain hydrocarbon containing from 2 to 10 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "alkyl" as used herein, means a straight or branched chain hydrocarbon containing from 1 to 10 carbon atoms, unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to $—CH_2—$, $—CH_2CH_2—$, $—CH_2CH_2CHC(CH_3)—$, $—CH_2CH(CH_2CH_3)CH_2—$.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl," as used herein, means a phenyl (i.e., monocyclic aryl), a bicyclic ring system containing at least one phenyl ring or an aromatic bicyclic ring containing only carbon atoms in the aromatic bicyclic ring system or a multicyclic aryl ring system, provided that the bicyclic or multicyclic aryl ring system does not contain a heteroaryl ring when fully aromatic. The bicyclic aryl can be azulenyl, naphthyl, or a phenyl (base ring) fused to a monocyclic cycloalkyl, a monocyclic cycloalkenyl, or a monocyclic heterocyclyl. The bicyclic aryl is attached to the parent molecular moiety through any carbon atom contained within the base ring, or any carbon atom with the napthyl or azulenyl ring. Representative examples of the bicyclic aryls include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2,3-dihydrobenzo[b][1,4]dioxan-5-yl, and 2,3-dihydrobenzo[b][1,4]dioxan-6-yl. In certain embodiments, the bicyclic aryl is (i) naphthyl or (ii) a phenyl ring fused to either a 5 or 6 membered monocyclic cycloalkyl, a 5 or 6 membered monocyclic cycloalkenyl, or a 5 or 6 membered monocyclic heterocyclyl. Multicyclic aryl groups are a phenyl ring (base ring) fused to either (i) one ring system selected from the group consisting of a bicyclic aryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic cycloalkyl, a monocyclic or bicyclic cycloalkenyl, and a monocyclic or bicyclic heterocyclyl, provided that when the base ring is fused to a bicyclic cycloalkyl, bicyclic cycloalkenyl, or bicyclic heterocyclyl, then the base ring is fused to the base ring of the a bicyclic cycloalkyl, bicyclic cycloalkenyl, or bicyclic heterocyclyl. The multicyclic aryl is attached to the parent molecular moiety through any carbon atom contained within the base ring. In certain embodiments, multicyclic aryl groups are a phenyl ring (base ring) fused to either (i) one ring system selected from the group consisting of a bicyclic aryl, a bicyclic cycloalkyl, a bicyclic cycloalkenyl, and a bicyclic heterocyclyl; or (ii) two other ring systems independently selected from the group consisting of a phenyl, a monocyclic cycloalkyl, a monocyclic cycloalkenyl, and a monocyclic heterocyclyl, provided that when the base ring is fused to a bicyclic cycloalkyl, bicyclic cycloalkenyl, or bicyclic heterocyclyl, then the base ring is fused to the base ring of the a bicyclic cycloalkyl, bicyclic cycloalkenyl, or bicyclic heterocyclyl. Examples of multicyclic aryl groups include but are not limited to anthracen-9-yl, phenanthren-9-yl, 1,2,3,4,5,6,7,8-octahydroanthracen-9-yl, 1,2,3,4-tetrahydroanthracen-5-yl, and 2,3-dihydronaphtho[2,3-b][1,4]dioxin-7-yl.

The term “arylalkyl” and “-alkylaryl” as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term “aryl-aryl,” as used herein, means an aryl group, as defined here, appended to the parent molecular moiety through an aryl group, as defined herein. Representative examples of aryl-aryl include, but are not limited to, biphenylyl.

The term “aryl-heteroaryl,” as used herein, means an aryl group, as defined here, appended to the parent molecular moiety through a heteroaryl group, as defined herein. Representative examples of aryl-heteroaryl include, but are not limited to, 4-phenyl-pyridin-2-yl and 2-phenyl-imidazol-1-yl.

The term “aryl-heterocyclyl,” as used herein, means an aryl group, as defined here, appended to the parent molecular moiety through an heterocyclyl group, as defined herein. Representative examples of aryl-heterocyclyl include, but are not limited to, 4-phenyl-piperazin-1-yl and 2-phenyl-pyrrolidin-1-yl.

The term “azido” as used herein means a $—N_3$ group.

The terms “cyano” and “nitrile” as used herein, mean a —CN group.

The term “cycloalkyl” as used herein, means a monocyclic, bicyclic, or a multicyclic cycloalkyl ring system. Monocyclic ring systems are cyclic hydrocarbon groups containing from 3 to 8 carbon atoms, where such groups can be saturated (i.e., cycloalkanyl) or unsaturated (i.e., cycloalkenyl), but not aromatic. Examples of monocyclic cycloalkyls include cyclopropyl, cyclobutyl, cyclopentyl, cyclopentenyl, cyclohexyl, cyclohexenyl, cycloheptyl, and cyclooctyl. In certain embodiments, monocyclic cycloalkyl groups are fully saturated. Bicyclic cycloalkyl groups are a monocyclic cycloalkyl ring (base ring) fused to one ring selected from the group consisting of a phenyl ring, a monocyclic cycloalkyl, a monocyclic cycloalkenyl, a monocyclic heterocyclyl, and a monocyclic heteroaryl. The bicyclic cycloalkyl is attached to the parent molecular moiety through any carbon atom contained within the base ring. In certain embodiments, bicyclic cycloalkyl groups are a monocyclic cycloalkyl ring (base ring) fused to one ring selected from the group consisting of a phenyl ring, a 5 or 6 membered monocyclic cycloalkyl, a 5 or 6 membered monocyclic cycloalkenyl, a 5 or 6 membered monocyclic heterocyclyl, and a 5 or 6 membered monocyclic heteroaryl. Multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other rings systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic cycloalkyl is attached to the parent molecular moiety through any carbon atom contained within the base ring. In certain embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other rings systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

“Cycloalkenyl” as used herein refers to a monocyclic, bicyclic, or a multicyclic cycloalkenyl ring system. Monocyclic ring systems are cyclic hydrocarbon groups containing from 3 to 8 carbon atoms, where such groups are unsaturated (i.e., containing at least one annular carbon-carbon double bond), but not aromatic. Examples of monocyclic ring systems include cyclopentenyl and cyclohexenyl. Bicyclic cycloalkenyl groups are a monocyclic cycloalkenyl ring (base ring) fused to one ring selected from the group consisting of a phenyl ring, a monocyclic cycloalkyl, a monocyclic cycloalkenyl, a monocyclic heterocyclyl, and monocyclic heteroaryl. The bicyclic cycloalkenyl is attached to the parent molecular moiety through any carbon atom contained within the base ring. In certain embodiments, bicyclic cycloalkenyl groups are a monocyclic cycloalkenyl ring (base ring) fused to one ring selected from the group consisting of a phenyl ring, a 5 or 6 membered monocyclic cycloalkyl, a 5 or 6 membered monocyclic cycloalkenyl, a 5 or 6 membered monocyclic heterocyclyl, and a 5 or 6 membered monocyclic heteroaryl. Multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two rings systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic cycloalkenyl is attached to the parent molecular moiety through any carbon atom contained within the base ring. IN certain embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two rings systems independently selected from the group consisting of a phenyl, a monocyclic heteroaryl, a monocyclic cycloalkyl, a monocyclic cycloalkenyl, and a monocyclic heterocyclyl.

The term "halo" or "halogen" as used herein, means —Cl, —Br, —I or —F.

The term "heteroaryl," as used herein, means a monocyclic, bicyclic, or a multicyclic heteroaryl ring system. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl ring (base ring) fused to a phenyl, a monocyclic cycloalkyl, a monocyclic cycloalkenyl, a monocyclic heterocyclyl, or a monocyclic heteroaryl. When the bicyclic heteroaryl contains a fused cycloalkyl, cycloalkenyl, or heterocyclyl ring, then the bicyclic heteroaryl group is connected to the parent molecular moiety through any carbon atom or nitrogen atom contained within the base ring. When the bicyclic heteroaryl is a monocyclic heteroaryl fused to a phenyl ring or a monocyclic heteroaryl, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, and thienopyridinyl. In certain embodiments, the bicyclic heteroaryl is a 5 or 6 membered monocyclic heteroaryl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl. The multicyclic heteroaryl group is a monocyclic heteroaryl ring (base ring) fused to either (i) one ring system selected from the group consisting of a bicyclic aryl, a bicyclic heteroaryl, a bicyclic heterocyclyl, a bicyclic cycloalkenyl, and a bicyclic cycloalkyl; or (ii) two ring systems selected from the group consisting of a phenyl, a bicyclic aryl, a monocyclic or bicyclic heteroaryl, a monocyclic or bicyclic heterocyclyl, a monocyclic or bicyclic cycloalkenyl, and a monocyclic or bicyclic cycloalkyl. The multicyclic heteroaryl group is connected to the parent molecular moiety through any carbon atom or nitrogen atom contained within the base ring. In certain embodiments, multicyclic heteroaryl groups are a monocyclic heteroaryl ring (base ring) fused to either (i) one ring system selected from the group consisting of a bicyclic aryl, a bicyclic heteroaryl, a bicyclic heterocyclyl, a bicyclic cycloalkenyl, and a bicyclic cycloalkyl; or (ii) two ring systems selected from the group consisting of a phenyl, a monocyclic heteroaryl, a monocyclic heterocyclyl, a monocyclic cycloalkenyl, and a monocyclic cycloalkyl. Examples of multicyclic heteroaryls include, but are not limited to 5H-[1,2,4]triazino[5,6-b]indol-5-yl, 2,3,4,9-tetrahydro-1H-carbazol-9-yl, 9H-pyrido[3,4-b]indol-9-yl, 9H-carbazol-9-yl, acridin-9-yl, The term "heteroarylalkyl" and "-alkylheteroaryl" as used herein, means a heteroaryl, as defined herein, appended to the parent molecular moiety through an alkyl group, as defined herein. Representative examples of heteroarylalkyl include, but are not limited to, fur-3-ylmethyl, 1H-imidazol-2-ylmethyl, 1H-imidazol-4-ylmethyl, 1-(pyridin-4-yl)ethyl, pyridin-3-ylmethyl, pyridin-4-ylmethyl, pyrimidin-5-ylmethyl, 2-(pyrimidin-2-yl)propyl, thien-2-ylmethyl, and thien-3-ylmethyl.

The term "heteroaryl-aryl," as used herein, means a heteroaryl group, as defined here, appended to the parent molecular moiety through an aryl group, as defined herein. Representative examples of heteroaryl-aryl include, but are not limited to, 4-pyridin-2-ylphenyl and 2-(imidazol-1-yl)phenyl.

The term "aryl-heterocyclyl," as used herein, means an aryl group, as defined here, appended to the parent molecular moiety through an heterocyclyl group, as defined herein. Representative examples of aryl-heterocyclyl include, but are not limited to, 4-phenyl-piperazin-1-yl and 2-phenyl-pyrrolidin-1-yl.

The term "heterocyclyl" as used herein, means a monocyclic, bicyclic, or multicyclic heterocycle. The monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, thiopyranyl, and trithianyl. The bicyclic heterocycle is a monocyclic heterocycle ring (base ring) fused to a phenyl, a monocyclic cycloalkyl, a monocyclic cycloalkenyl, a monocyclic heterocycle, or a monocyclic heteroaryl. The bicyclic heterocycle is connected to the parent molecular moiety through any carbon atom or any nitrogen atom contained within the base ring. In certain embodiments, bicyclic heterocycles are a monocyclic heterocycle ring (base ring) fused to a phenyl, a 5 or 6 membered monocyclic cycloalkyl, a 5 or 6 membered monocyclic cycloalkenyl, a 5 or 6 membered monocyclic heterocycle, or a 5 or 6 membered monocyclic heteroaryl. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other rings systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In certain embodiments, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other rings systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, 10H-phenoxazin-10-yl, 10,11-dihydro-5H-dibenzo[b,f]azepin-5-yl, 1,2,3,4-tetrahydropyrido[4,3-g]isoquinolin-2-yl, 12H-benzo[b]phenoxazin-12-yl, and dodecahydro-1H-carbazol-9-yl.

The term "heterocyclyl-aryl," as used herein, means a heterocyclyl group, as defined here, appended to the parent molecular moiety through an aryl group, as defined herein. Representative examples of heterocyclyl-aryl include, but are not limited to, 4-(piperazin-1-yl)phenyl and 3-(pyrrolidin-1-yl)phenyl.

The term "nitro" as used herein, means a $—NO_2$ group.

The term "nitroso" as used herein, means a —NO group.

The term "oxo" as used herein means a =O group.

The term "saturated" as used herein means the referenced chemical structure does not contain any multiple carbon-carbon bonds. For example, a saturated cycloalkyl group as defined herein includes cyclohexyl, cyclopropyl, and the like.

The term "thia" as used herein means a =S group.

The term "unsaturated" as used herein means the referenced chemical structure contains at least one multiple carbon-carbon bond, but is not aromatic. For example, an unsaturated cycloalkyl group as defined herein includes cyclohexenyl, cyclopentenyl, cyclohexadienyl, and the like.

As used herein, the term "cell" is meant to refer to a cell that is in vitro, ex vivo, or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" a cell with a compound includes the administration of a compound described herein to an individual or patient, such as a human, as well as, introducing a compound into a sample containing a cellular or purified preparation.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used here, a subject "in need thereof" refers to a subject that has the disorder or disease to be treated or is predisposed to developing the disease or disorder.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician, which includes one or more of the following:

(1) limiting development of the disease; for example, slowing or halting development of a disease, condition or disorder in an individual who may be predisposed to the disease, condition or disorder but does not yet experience or display the pathology or symptomatology of the disease;

(2) inhibiting the disease; for example, inhibiting a disease, condition or disorder in an individual who is experiencing or displaying the pathology or symptomatology of the disease, condition or disorder; and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

As used here, the terms "treatment" and "treating" means (i) ameliorating the referenced disease state, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease; or (ii) eliciting the referenced biological effect.

As used herein, the phrase "pharmaceutically acceptable salt" refers to both pharmaceutically acceptable acid and base addition salts and solvates. Such pharmaceutically acceptable salts include salts of acids such as hydrochloric, phosphoric, hydrobromic, sulfuric, sulfinic, formic, fumaric, toluenesulfonic, methanesulfonic, nitric, benzoic, citric, tartaric, maleic, hydroiodic, alkanoic such as acetic, $HOOC—(CH_2)_n—COOH$ where n is 0-4, and the like. Non-toxic pharmaceutical base addition salts include salts of bases such as sodium, potassium, calcium, ammonium, and the like. Those skilled in the art will recognize a wide variety of non-toxic pharmaceutically acceptable addition salts.

As used herein, the phrase "pharmaceutically acceptable anion" refers to anionic groups which are tolerated in vivo, such as, but not limited to, halides (fluoride, chloride, bromide, iodide), phosphate, sulfate, sulfinate, formate, fumarate, toluenesulfonate, methanesulfonate, nitrate, benzoate, citrate, tartarate, maleate, alkanoates such as acetate.

The term "prodrug" as used herein, refers to a pharmacologically inactive derivative of a parent "drug" molecule that requires biotransformation (e.g., either spontaneous or enzymatic) within the target physiological system to release, or to convert (e.g., enzymatically, physiologically, mechanically, electromagnetically) the prodrug into the active drug. Prodrugs are designed to overcome problems associated with stability, water solubility, toxicity, lack of specificity, or limited bioavailability. Exemplary prodrugs comprise an active drug molecule itself and a chemical masking group (e.g., a group that reversibly suppresses the activity of the drug). Some prodrugs are variations or derivatives of compounds that have groups cleavable under metabolic conditions. Prodrugs can be readily prepared from the parent compounds using methods known in the art, such as those described in A Textbook of Drug Design and Development, Krogsgaard-Larsen and H. Bundgaard (eds.), Gordon & Breach, 1991, particularly Chapter 5: "Design and Applications of Prodrugs"; Design of Prodrugs, H. Bundgaard (ed.), Elsevier, 1985; Prodrugs: Topical and Ocular Drug Delivery, K. B. Sloan (ed.), Marcel Dekker, 1998; Methods in Enzymology, K. Widder et al. (eds.), Vol. 42, Academic Press, 1985, particularly pp. 309-396; Burger's Medicinal Chemistry and Drug Discovery, 5th Ed., M. Wolff (ed.), John Wiley & Sons, 1995, particularly Vol. 1 and pp. 172-178 and pp. 949-982; Pro-Drugs as Novel Delivery Systems, T. Higuchi and V. Stella (eds.), Am. Chem. Soc., 1975; and Bioreversible Carriers in Drug Design, E. B. Roche (ed.), Elsevier, 1987.

Exemplary prodrugs become pharmaceutically active in vivo or in vitro when they undergo solvolysis under physiological conditions or undergo enzymatic degradation or other biochemical transformation (e.g., phosphorylation, hydrogenation, dehydrogenation, glycosylation). Prodrugs often offer advantages of water solubility, tissue compatibility, or delayed release in the mammalian organism. (See e.g., Bundgard, Design of Prodrugs, pp. 7-9, 21-24, Elsevier, Amsterdam (1985); and Silverman, The Organic Chemistry of Drug Design and Drug Action, pp. 352-401, Academic Press, San Diego, CA (1992)). Common prodrugs include acid derivatives such as esters prepared by reaction of parent acids with a suitable alcohol (e.g., a lower alkanol) or esters prepared by reaction of parent alcohol with a suitable carboxylic acid, (e.g., an amino acid), amides prepared by reaction of the parent acid compound with an amine, basic groups reacted to form an acylated base derivative (e.g., a lower alkylamide), or phosphorus-containing derivatives, e.g., phosphate, phosphonate, and phosphoramidate esters, including cyclic phosphate, phosphonate, and phosphoramidate (see, e.g., US Patent Application Publication No. US 2007/0249564 A1; herein incorporated by reference in its entirety).

DETAILED DESCRIPTION OF THE INVENTION

Experiments conducted during the course of developing embodiments for the present invention demonstrated that specific small-molecules having a quindoline (or similar) structure described herein displayed significant anti-herpes simplex virus-1 (anti-HSV-1) activity. In particular, it was shown that in displaying significant anti-HSV-1 activity the compound GSA-0932

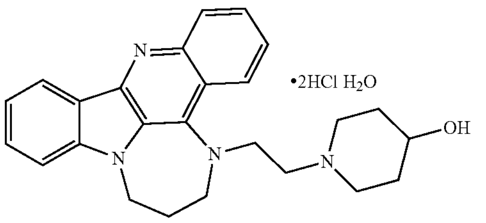

•2HCl $H_2O$

GSA0932

Chemical Formula: C25H28N4O 2HCl H2O$C_{25}H_{28}N_4O$ ( Molecular Weight: 409.8241400.53 )

acted in early events of the viral life cycle, greatly stabilized the HSV-1 G-quadruplex structures, and binded G-quadruplexes with a preference for the HSV-1 G-quadruplexes vs the telomeric sequence.

As such, the present invention relates to use of a class of small-molecules having a quindoline (or similar) structure having significant anti-HSV activity. In particular, the present invention provides methods for inhibiting viral activity (e.g., HSV activity) and/or expression through stabilization of G-quadruplex structures related to viral activity and/or expression, and methods for treating any type of condition characterized with viral activity (e.g., HSV activity).

Indeed, the present invention provides methods of treating, suppressing, inhibiting, reducing an incidence, reducing the pathogenesis of, ameliorating the symptoms of, or ameliorating the secondary symptoms of a primary or recurring Herpes Simplex Virus (HSV) infection, or prolonging the latency to a relapse of an HSV infection, and disorders and symptoms associated with same in a subject comprising the step of contacting the subject with a composition comprising a small molecule having a quindoline (or similar) structure having significant anti-HSV activity.

For example, in some embodiments, the inhibition of viral activity and/or expression (e.g., HSV activity and/or expression) occurs through, for example, stabilization of G-quadruplex structures related to such viral activity and/or expression. The present invention contemplates that such viral antagonists satisfy an unmet need for the treatment of multiple viral conditions (e.g., conditions related to HSV activity and/or expression), either when administered as monotherapy, or when administered in a temporal relationship with additional agent(s), such as other anti-viral therapies.

The methods of the present invention are useful for the treatment, amelioration, or prevention of any type of condition characterized with activity related to unstable G-quadruplex structures disorders (e.g., viral conditions (e.g., viral conditions related to HSV activity)).

In certain embodiments, the present invention provides methods/uses for the treatment, amelioration, or prevention of viral disorders (e.g., viral disorders related to HSV activity) through administration of specific quindoline (or similar) compounds. In certain embodiments, the compounds can be used to treat, ameliorate, or prevent a viral condition that is characterized by resistance to viral therapies. In certain embodiments, the viral condition is any type of viral condition characterized with unstable G-quadruplex activity.

Such methods and uses are not limited to specific quindoline compounds.

In some embodiments, the specific quindoline compounds encompassed within Formula I are utilized:

(Formula I)

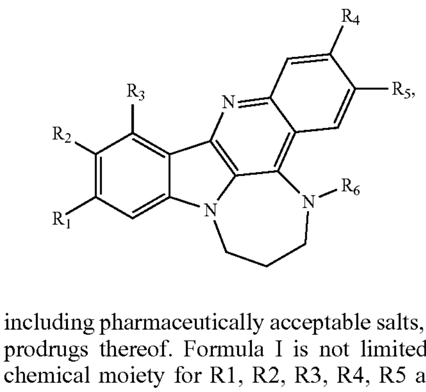

including pharmaceutically acceptable salts, solvates, and/or prodrugs thereof. Formula I is not limited to a particular chemical moiety for R1, R2, R3, R4, R5 and R6. In some embodiments, the particular chemical moiety for R1, R2, R3, R4, R5 and R6 independently include any chemical moiety that permits the resulting compound to stabilize G-quadruplex structures.

In some embodiments, the particular chemical moiety for R1, R2, R3, R4, R5 and R6 independently include any chemical moiety that permits the resulting compound to inhibit HSV-1 activity and/or expression. In some embodiments, the particular chemical moiety for R1, R2, R3, R4, R5 and R6 independently include any chemical moiety that permits the resulting compound to inhibit HSV activity and/or expression through stabilization of G-quadruplex structures related to HSV activity and/or expression.

In some embodiments, R1 is hydrogen or methyl.

In some embodiments, R2 is hydrogen,

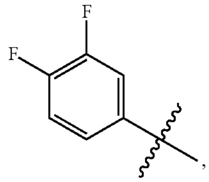
,
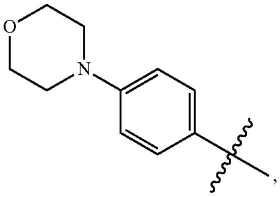
,
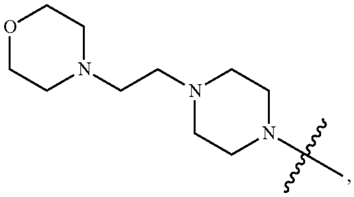
,
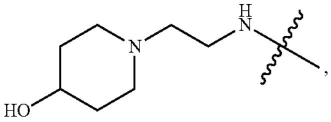
, and
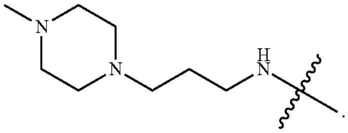
.

In some embodiments, R3 is hydrogen or methyl.

In some embodiments, R4 is selected from hydrogen,

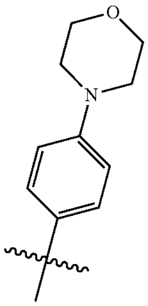
,
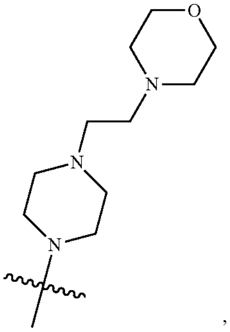
,
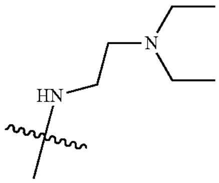
,
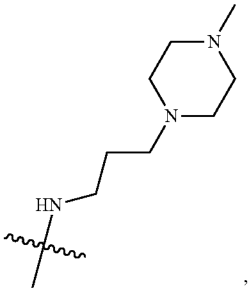
,

-continued

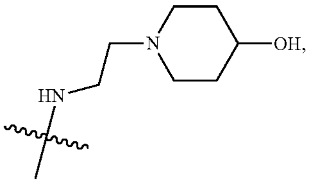
,
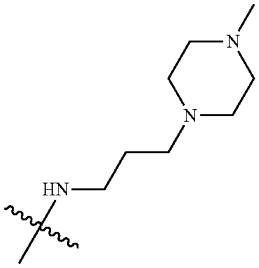
,
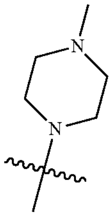
,
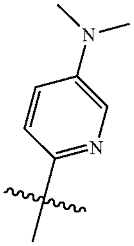
,
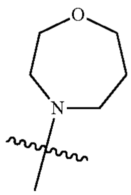
,
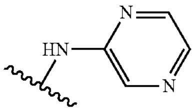
,
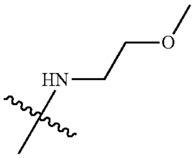
,
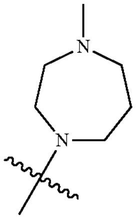
,
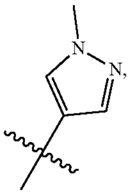
,
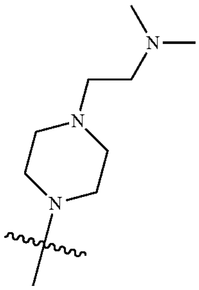
,
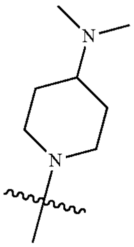
,
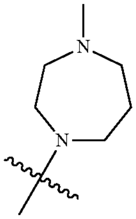
,
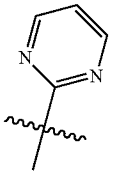
,
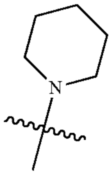
, and -continued
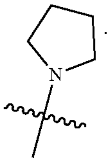
In some embodiments, R5 is selected from Hydrogen, halogen (e.g., Chlorine, Bromine),
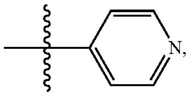
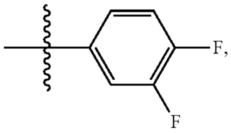
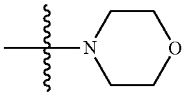
and
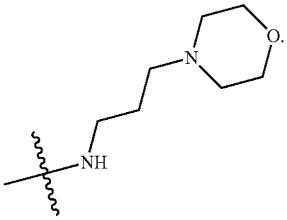
In some embodiments, R6 is selected from
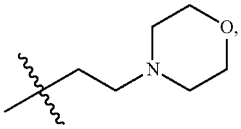
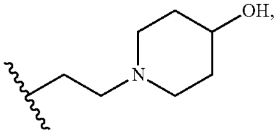
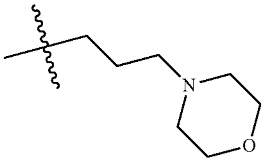
,
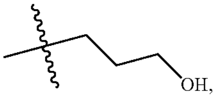
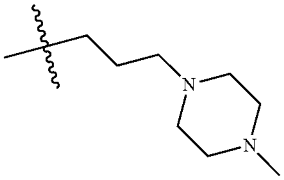
,
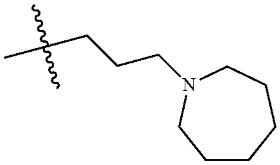
,
-continued
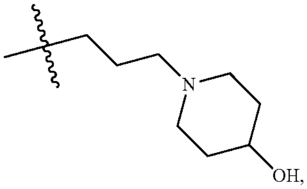
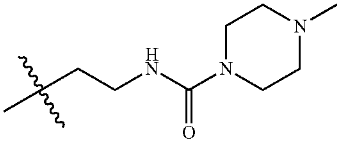
,
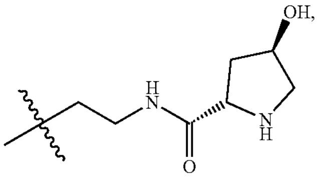
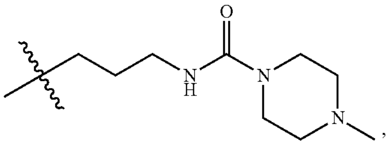
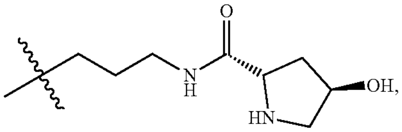
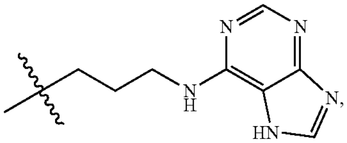
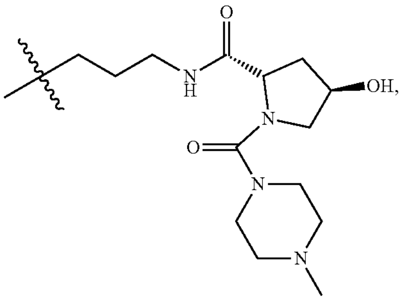
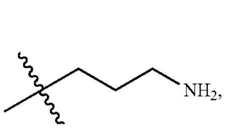
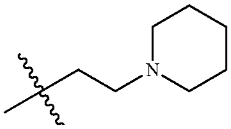
,
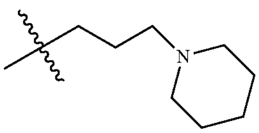
,
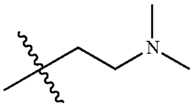
,
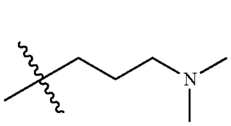
,
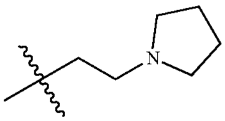
, -continued
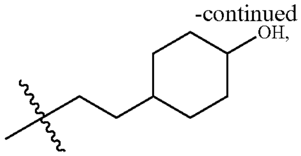
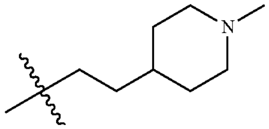
and,
-continued
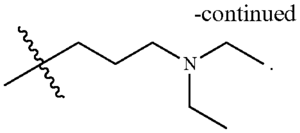
In some embodiments, compounds shown in Table I are contemplated for Formula I.
TABLE I
Structures of Quindoline compounds
| Compound Number | | Structure |
|---|---|---|
| 1 | GSA0817 | 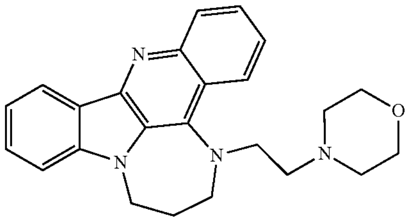 [SMILES: c1ccc2c3c4c(nc2c1)c1ccccc1n4CCCN3CCN1CCOCC1] |
| 2 | GSA0829 | 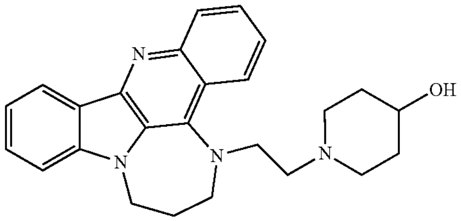 [SMILES: OC1CCN(CCN2CCCn3c4ccccc4c4nc5ccccc5c2c43)CC1] |
| 3 | GSA0825 | 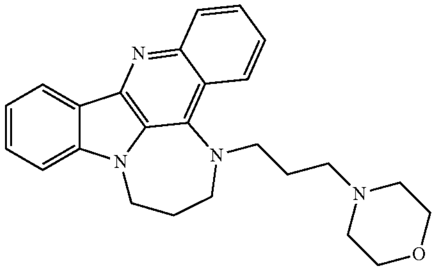 [SMILES: c1ccc2c3c4c(nc2c1)c1ccccc1n4CCCN3CCCN1CCOCC1] |
| 4 | GSA0826 | 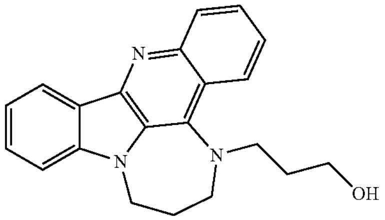 [SMILES: OCCCN1CCCn2c3ccccc3c3nc4ccccc4c1c32] |

TABLE I-continued
| Structures of Quindoline compounds | | |
|---|---|---|
| Compound Number | | Structure |
| 5 | GSA0903 | 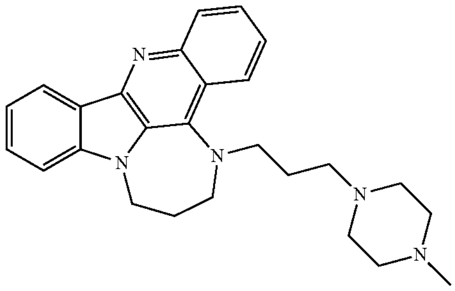 [SMILES: CN1CCN(CCCN2CCCn3c4ccccc4c4nc5ccccc5c2c43)CC1] |
| 6 | GSA0920 | 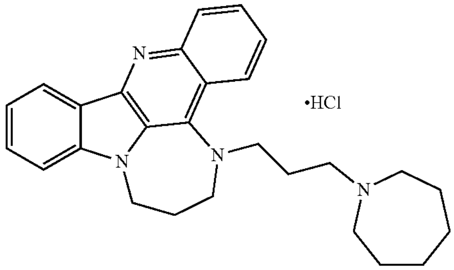 [SMILES: c1ccc2c3c4c(nc2c1)c1ccccc1n4CCCN3CCCN1CCCCCC1 ; Cl] •HCl |
| 7 | GSA0216 | 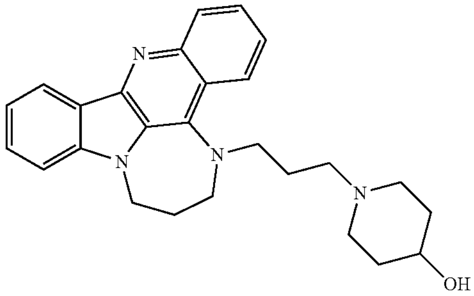 [SMILES: OC1CCN(CCCN2CCCn3c4ccccc4c4nc5ccccc5c2c43)CC1] |
| 8 | GSA0833 | 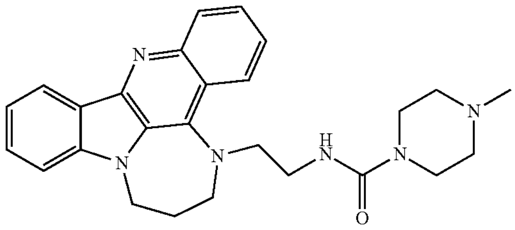 [SMILES: CN1CCN(C(=O)NCCN2CCCn3c4ccccc4c4nc5ccccc5c2c43)CC1] |
| 9 | GSA0843 | 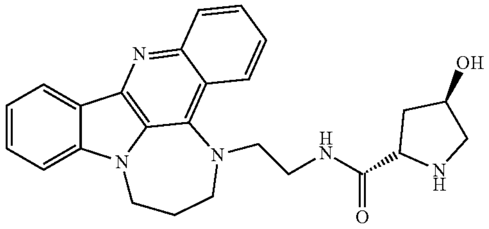 |

TABLE I-continued
| Structures of Quindoline compounds | | |
|---|---|---|
| Compound Number | | Structure |
| 10 | GSA0848 | 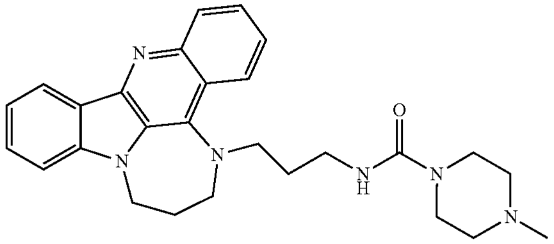 [SMILES: CN1CCN(C(=O)NCCCN2CCCn3c4ccccc4c4nc5ccccc5c2c43)CC1] |
| 11 | GSA0901 | 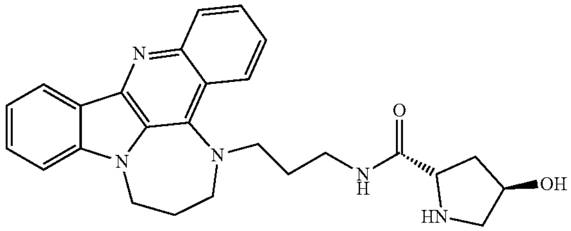 |
| 12 | GSA0926 | 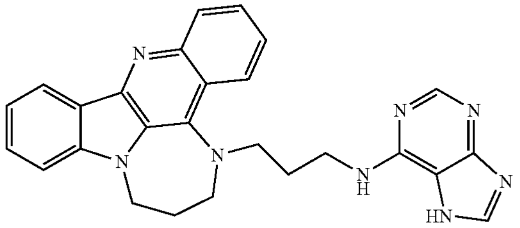 [SMILES: c1ccc2c3c4c(nc2c1)c1ccccc1n4CCCN3CCCNc1ncnc2nc[nH]c12] |
| 13 | GSA0921 | 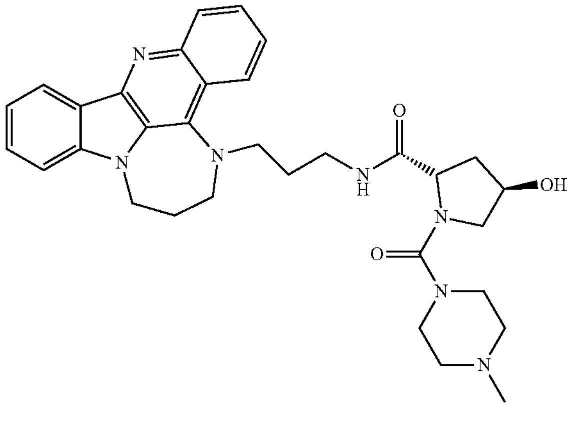 |
| 14 | GSA1141 | 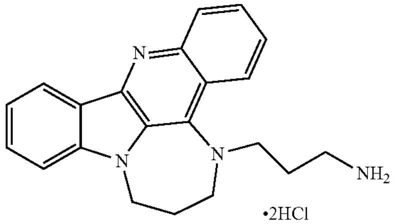 [SMILES: NCCCN1CCCn2c3ccccc3c3nc4ccccc4c1c32] •2HCl |

TABLE I-continued
| Structures of Quindoline compounds | | |
|---|---|---|
| Compound Number | | Structure |
| 15 | GSA1202 | 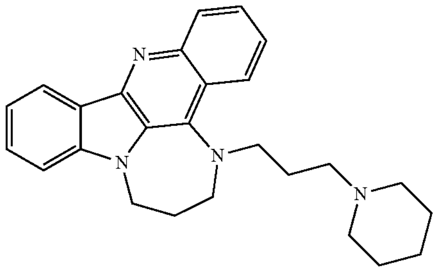 [SMILES: c1ccc2c3c4c(nc2c1)c1ccccc1n4CCCN3CCCN1CCCCC1] |
| 16 | GSA1204 | 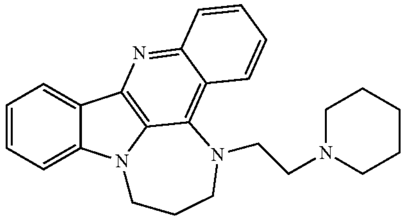 [SMILES: c1ccc2c3c4c(nc2c1)c1ccccc1n4CCCN3CCN1CCCCC1] |
| 17 | GSA0830 | 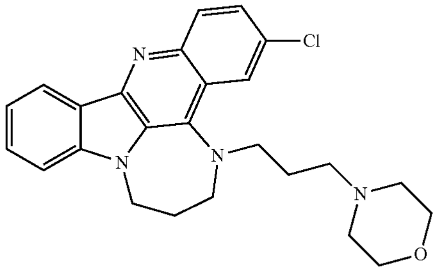 [SMILES: Clc1ccc2nc3c4ccccc4n4c3c(c2c1)N(CCCN1CCOCC1)CCC4] |
| 18 | GSA0844 | 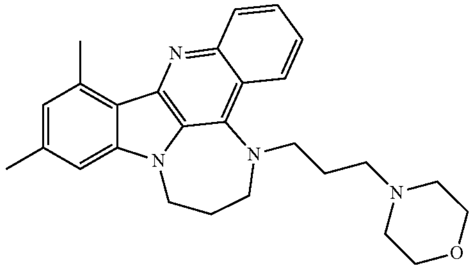 [SMILES: Cc1cc(C)c2c3nc4ccccc4c4c3n(c2c1)CCCN4CCCN1CCOCC1] |
| 19 | GSA0907 | 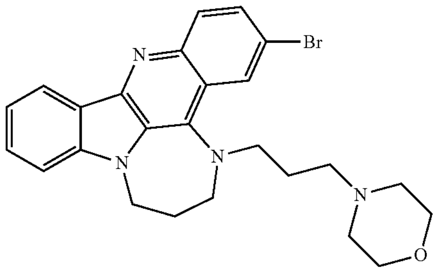 |

TABLE I-continued
| Structures of Quindoline compounds | | |
|---|---|---|
| Compound Number | | Structure |
| 20 | GSA1502 | 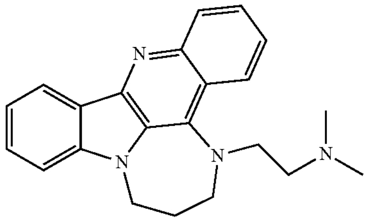 [SMILES: CN(C)CCN1CCCn2c3ccccc3c3nc4ccccc4c1c32] |
| 21 | GSA1504 | 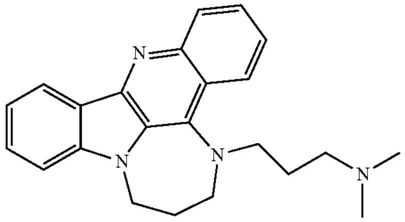 [SMILES: CN(C)CCCN1CCCn2c3ccccc3c3nc4ccccc4c1c32] |
| 22 | GSA1510 | 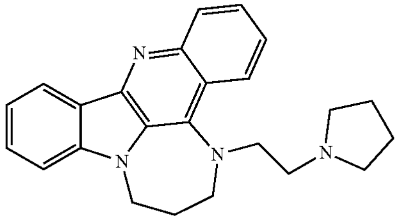 [SMILES: c1ccc2c3c4c(nc2c1)c1ccccc1n4CCCN3CCN1CCCC1] |
| 23 | GSA1512 | 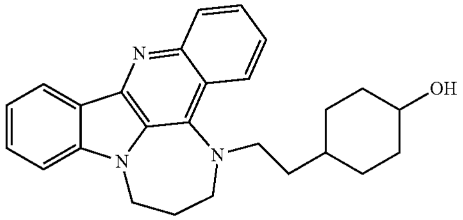 [SMILES: OC1CCC(CCN2CCCn3c4ccccc4c4nc5ccccc5c2c43)CC1] |
| 24 | GSA1508 | 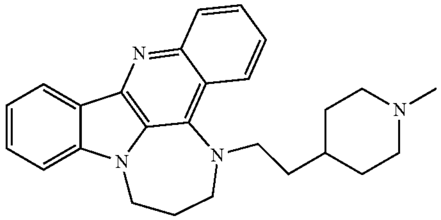 [SMILES: CN1CCC(CCN2CCCn3c4ccccc4c4nc5ccccc5c2c43)CC1] |
| 25 | GSA0114 | 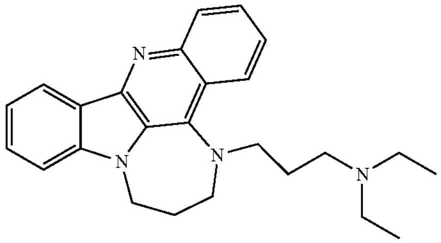 [SMILES: CCN(CC)CCCN1CCCn2c3ccccc3c3nc4ccccc4c1c32] |

TABLE I-continued
| Structures of Quindoline compounds | | |
|---|---|---|
| Compound Number | | Structure |
| 26 | GSA0932 | 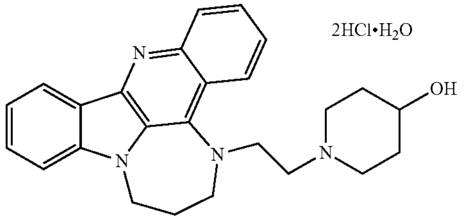 [SMILES: OC1CCN(CCN2CCCn3c4ccccc4c4nc5ccccc5c2c43)CC1 ; "2HCl·H2O"] 2HCl•$H_2O$ |
| 27 | GSA0905 | 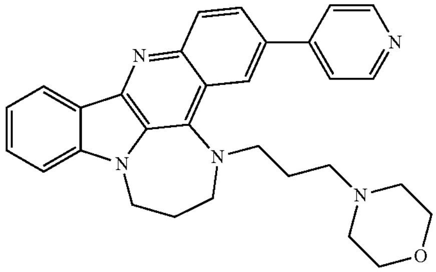 [SMILES: c1ccc2c(c1)c1nc3ccc(-c4ccncc4)cc3c3c1n2CCCN3CCCN1CCOCC1] |
| 28 | GSA0908 | 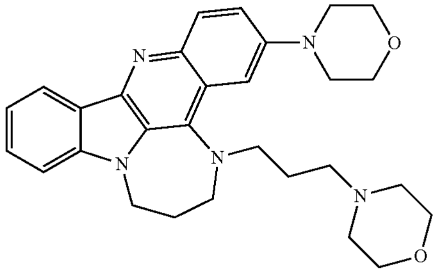 [SMILES: c1ccc2c(c1)c1nc3ccc(N4CCOCC4)cc3c3c1n2CCCN3CCCN1CCOCC1] |
| 29 | GSA1010 | 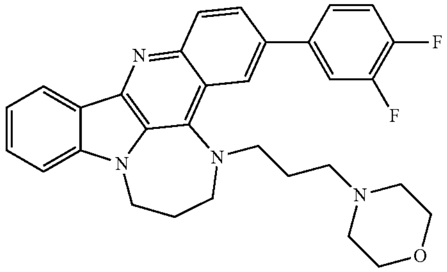 [SMILES: Fc1ccc(-c2ccc3nc4c5ccccc5n5c4c(c3c2)N(CCCN2CCOCC2)CCC5)cc1F] |
| 30 | GSA0257 | 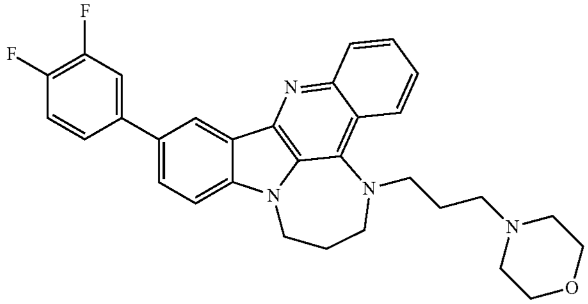 [SMILES: Fc1ccc(-c2ccc3c(c2)c2nc4ccccc4c4c2n3CCCN4CCCN2CCOCC2)cc1F] |

TABLE I-continued
| Structures of Quindoline compounds | | |
|---|---|---|
| Compound Number | | Structure |
| 31 | GSA1011 | 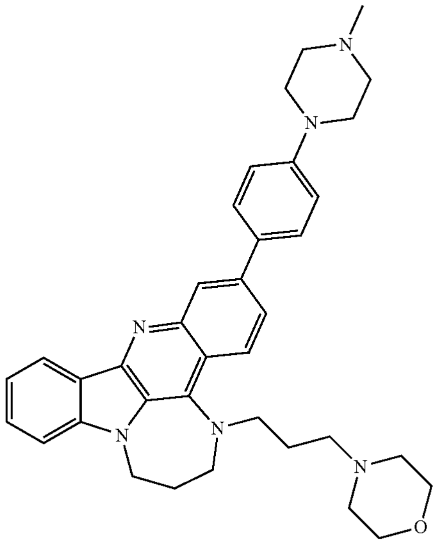 [SMILES: CN1CCN(c2ccc(-c3ccc4c5c6c(nc4c3)c3ccccc3n6CCCN5CCCN3CCOCC3)cc2)CC1] |
| 32 | GSA1014 | 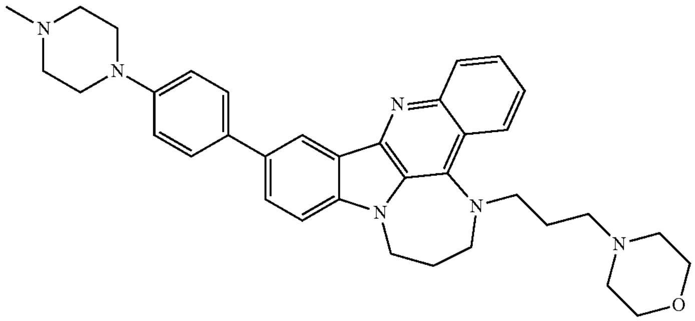 [SMILES: CN1CCN(c2ccc(-c3ccc4c(c3)c3nc5ccccc5c5c3n4CCCN5CCCN3CCOCC3)cc2)CC1] |
| 33 | GSA0923 | 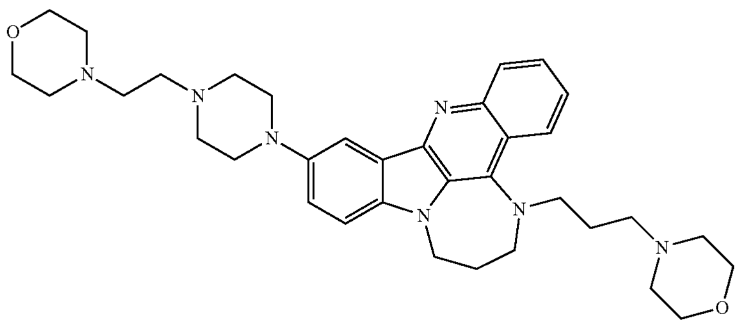 [SMILES: c1ccc2c3c4c(nc2c1)c1cc(N2CCN(CCN5CCOCC5)CC2)ccc1n4CCCN3CCCN1CCOCC1] |

TABLE I-continued
| Structures of Quindoline compounds | | |
|---|---|---|
| Compound Number | | Structure |
| 34 | GSA1108 | 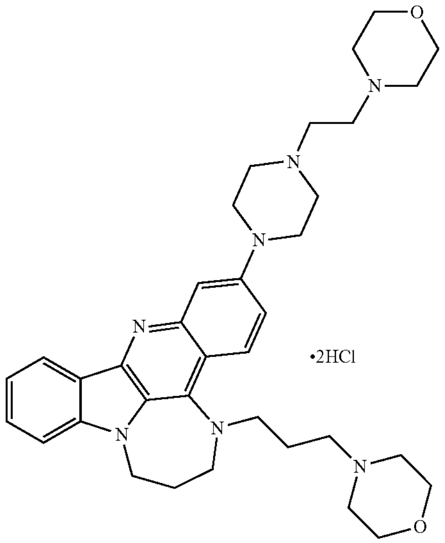 [SMILES: c1ccc2c(c1)c1nc3cc(N4CCN(CCN5CCOCC5)CC4)ccc3c3c1n2CCCN3CCCN1CCOCC1] |
| 35 | GSA0911 | 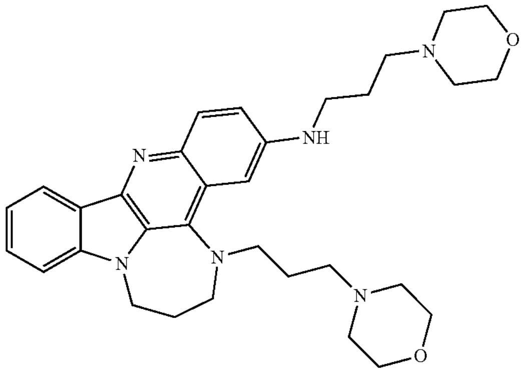 [SMILES: c1ccc2c(c1)c1nc3ccc(NCCCN4CCOCC4)cc3c3c1n2CCCN3CCCN1CCOCC1] |
| 36 | GSA1107 | 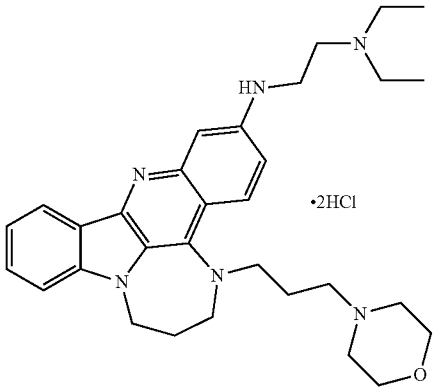 [SMILES: CCN(CC)CCNc1ccc2c3c4c(nc2c1)c1ccccc1n4CCCN3CCCN1CCOCC1] |

TABLE I-continued
| Structures of Quindoline compounds | | |
|---|---|---|
| Compound Number | | Structure |
| 37 | GSA1016 | 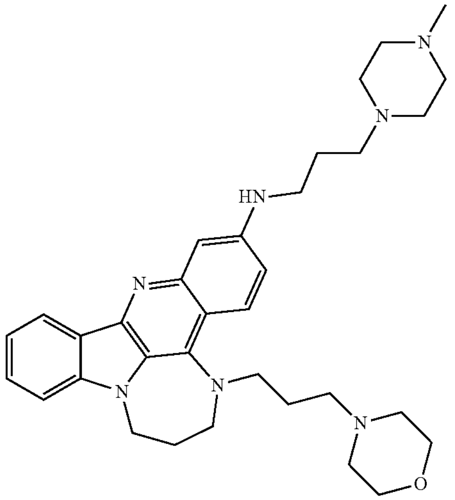 [SMILES: CN1CCN(CCCNc2ccc3c4c5c(nc3c2)c2ccccc2n5CCCN4CCCN2CCOCC2)CC1] |
| 38 | GSA0261 | 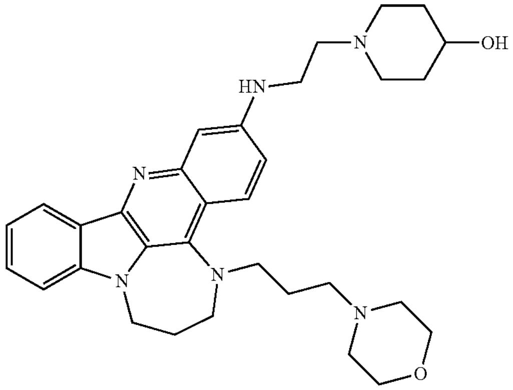 [SMILES: OC1CCN(CCNc2ccc3c4c5c(nc3c2)c2ccccc2n5CCCN4CCCN2CCOCC2)CC1] |
| 39 | GSA1021 | 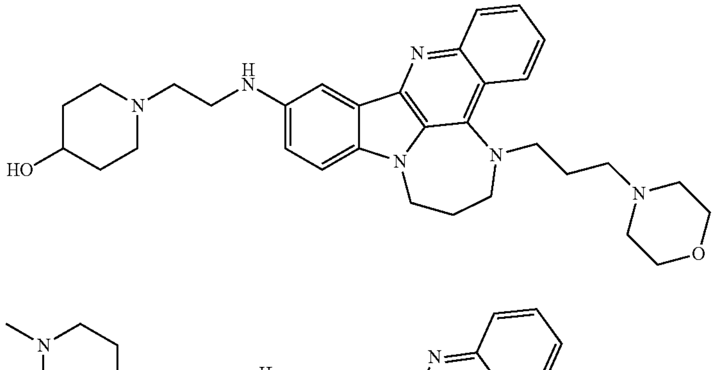 |
| 40 | GSA1104 | 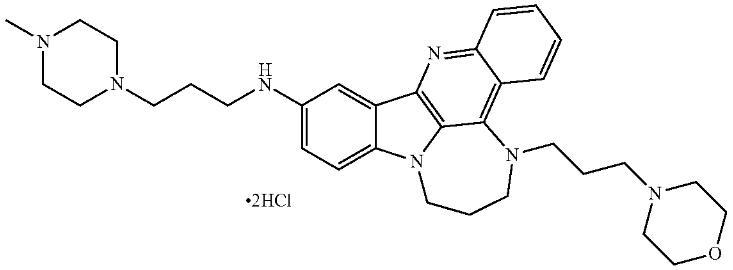 [SMILES: CN1CCN(CCCNc2ccc3c(c2)c2nc4ccccc4c4c2n3CCCN4CCCN2CCOCC2)CC1] •2HCl |

TABLE I-continued
Structures of Quindoline compounds
| Compound Number | | Structure |
|---|---|---|
| 41 | GSA1019 | 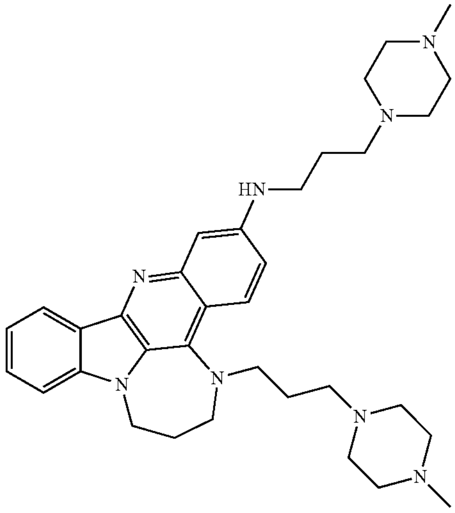 [SMILES: CN1CCN(CCCNc2ccc3c4c5c(nc3c2)c2ccccc2n5CCCN4CCCN2CCN(C)CC2)CC1] |
| 42 | GSA1018 | 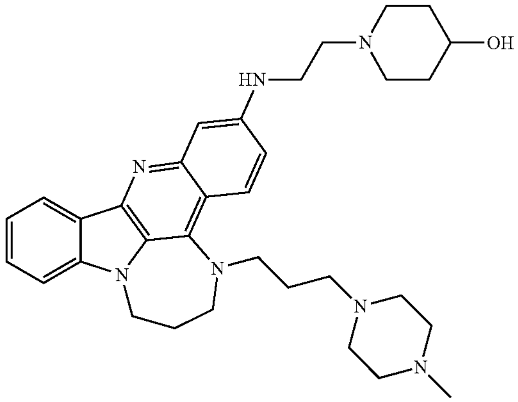 [SMILES: CN1CCN(CCCN2CCCn3c4ccccc4c4nc5cc(NCCN6CCC(O)CC6)ccc5c2c43)CC1] |
| 43 | GSA1109 | 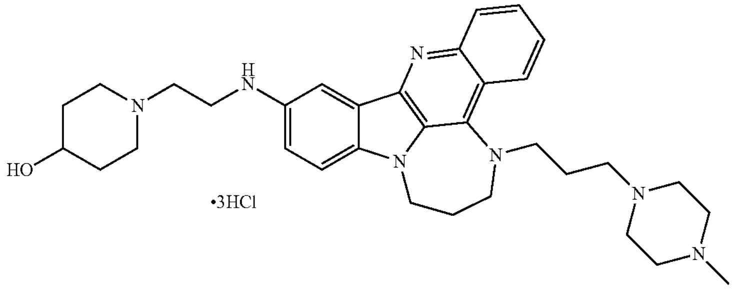 [SMILES: CN1CCN(CCCN2CCCn3c4ccc(NCCN5CCC(O)CC5)cc4c4nc5ccccc5c2c43)CC1] •3HCl |

TABLE I-continued
| Structures of Quindoline compounds | | |
|---|---|---|
| Compound Number | | Structure |
| 44 | GSA1110 | 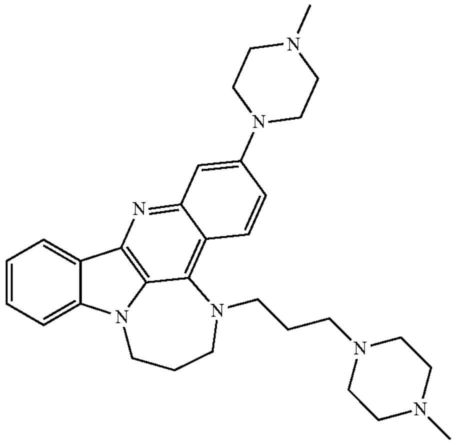 [SMILES: CN1CCN(CCCN2CCCn3c4ccccc4c4nc5cc(N6CCN(C)CC6)ccc5c2c43)CC1] |
| 45 | GSA1111 | 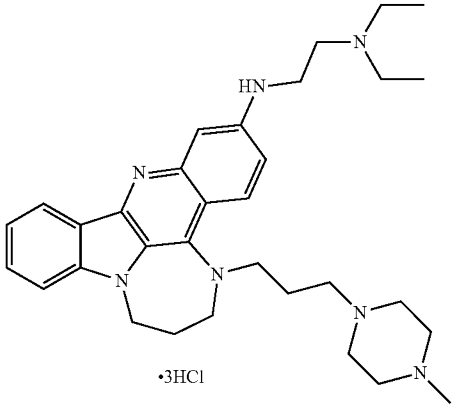 [SMILES: CCN(CC)CCNc1ccc2c3c4c(nc2c1)c1ccccc1n4CCCN3CCCN1CCN(C)CC1] •3HCl |
| 46 | GSA1102 | 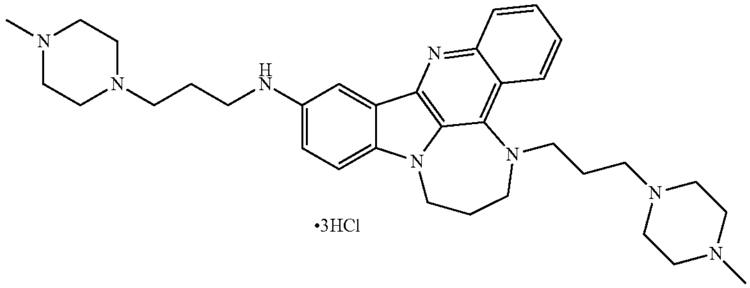 •3HCl |
| 47 | GSA1106 | 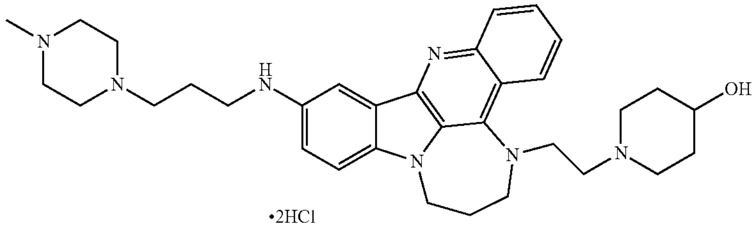 [SMILES: CN1CCN(CCCNc2ccc3c(c2)c2nc4ccccc4c4c2n3CCCN4CCN2CCC(O)CC2)CC1] •2HCl |

TABLE I-continued
| Structures of Quindoline compounds | | |
|---|---|---|
| Compound Number | | Structure |
| 48 | GSA1022 | 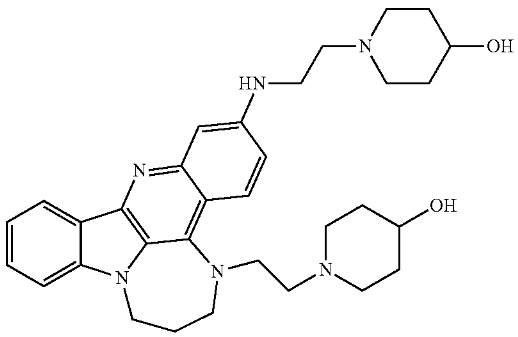 [SMILES: OC1CCN(CCNc2ccc3c4c5c(nc3c2)c2ccccc2n5CCCN4CCN2CCC(O)CC2)CC1] |
| 49 | GSA1103 | 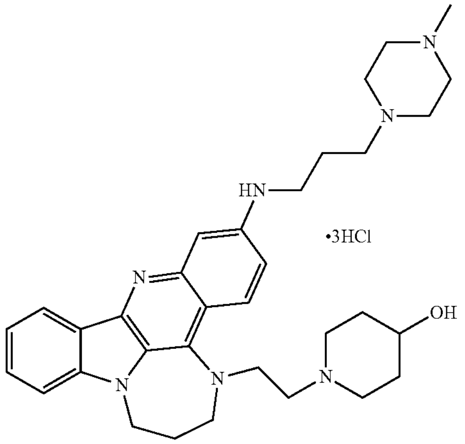 [SMILES: CN1CCN(CCCNc2ccc3c4c5c(nc3c2)c2ccccc2n5CCCN4CCN2CCC(O)CC2)CC1] |
| 50 | GSA0262 | 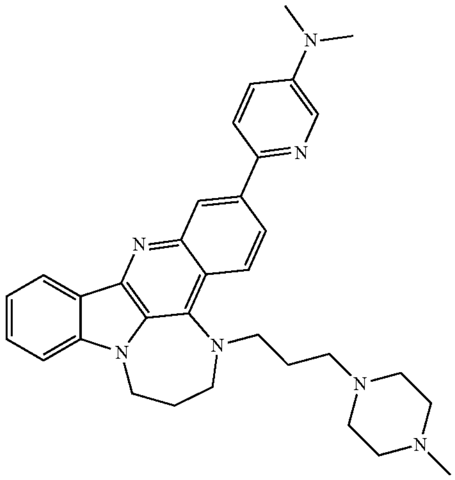 [SMILES: CN1CCN(CCCN2CCCn3c4ccccc4c4nc5cc(-c6ccc(N(C)C)cn6)ccc5c2c43)CC1] |

TABLE I-continued
| Structures of Quindoline compounds | | |
|---|---|---|
| Compound Number | | Structure |
| 51 | GSA1401 | 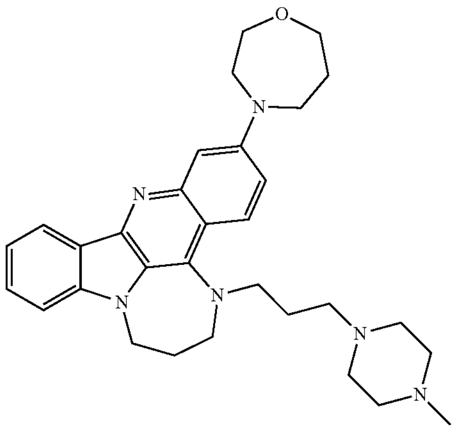 [SMILES: CN1CCN(CCCN2CCCn3c4ccccc4c4nc5cc(N6CCCOCC6)ccc5c2c43)CC1] |
| 52 | GSA1402 | 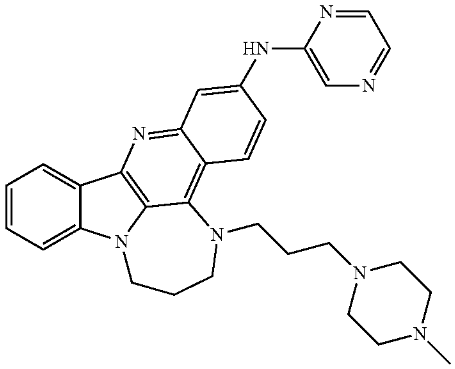 [SMILES: CN1CCN(CCCN2CCCn3c4ccccc4c4nc5cc(Nc6cnccn6)ccc5c2c43)CC1] |
| 53 | GSA1403 | 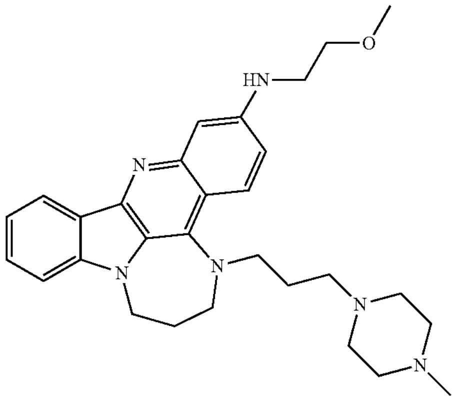 [SMILES: COCCNc1ccc2c3c4c(nc2c1)c1ccccc1n4CCCN3CCCN1CCN(C)CC1] |

TABLE I-continued
| Structures of Quindoline compounds | | |
|---|---|---|
| Compound Number | | Structure |
| 54 | GSA1501 | 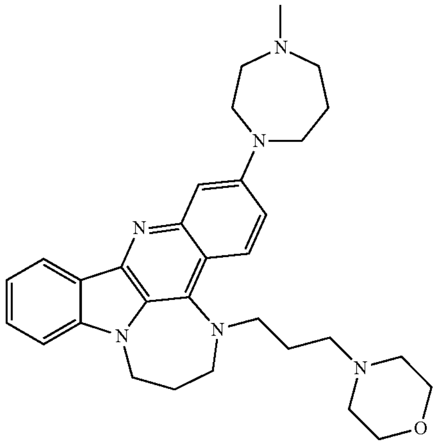 [SMILES: CN1CCCN(c2ccc3c4c5c(nc3c2)c2ccccc2n5CCCN4CCCN2CCOCC2)CC1] |
| 55 | GSA1503 | 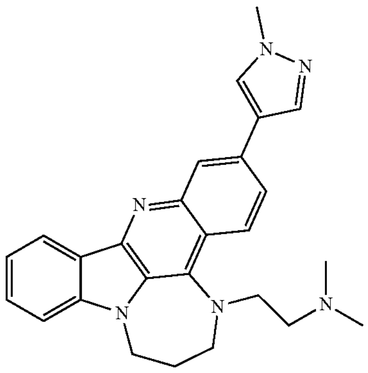 [SMILES: CN(C)CCN1CCCn2c3ccccc3c3nc4cc(-c5cnn(C)c5)ccc4c1c32] |
| 56 | GSA1505 | 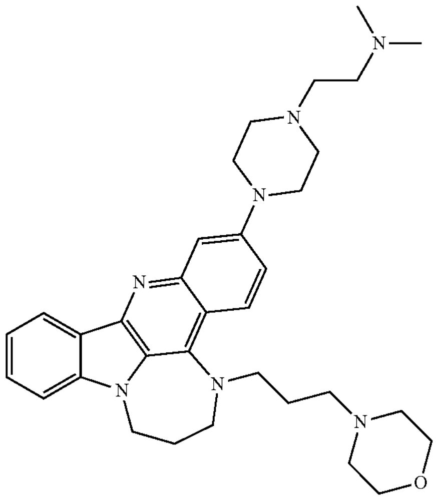 [SMILES: CN(C)CCN1CCN(c2ccc3c4c5c(nc3c2)c2ccccc2n5CCCN4CCCN2CCOCC2)CC1] |

TABLE I-continued
| Structures of Quindoline compounds | | |
|---|---|---|
| Compound Number | | Structure |
| 57 | GSA1509 | 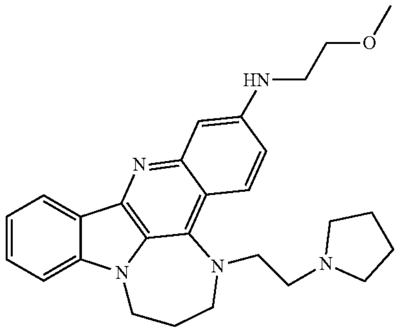 [SMILES: COCCNc1ccc2c3c4c(nc2c1)c1ccccc1n4CCCN3CCN1CCCC1] |
| 58 | GSA1511 | 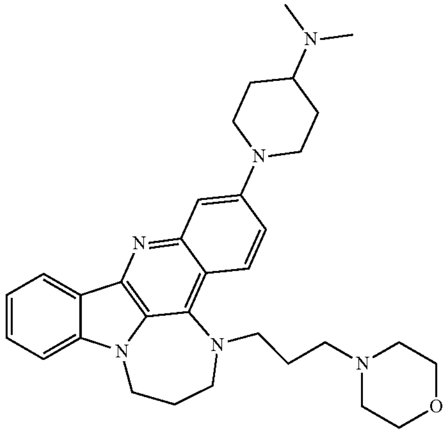 [SMILES: CN(C)C1CCN(c2ccc3c4c5c(nc3c2)c2ccccc2n5CCCN4CCCN2CCOCC2)CC1] |
| 59 | GSA1205 | 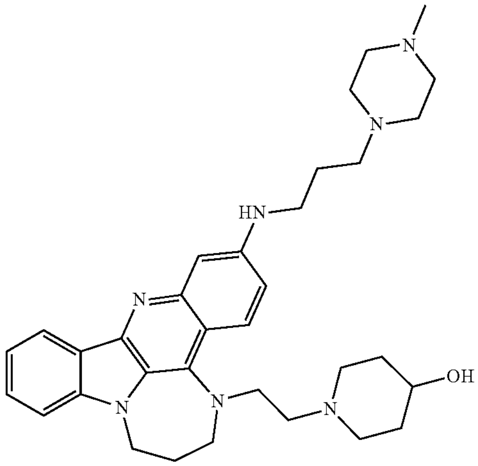 [SMILES: CN1CCN(CCCNc2ccc3c4c5c(nc3c2)c2ccccc2n5CCCN4CCN2CCC(O)CC2)CC1] |

TABLE I-continued
| Structures of Quindoline compounds | | |
|---|---|---|
| Compound Number | | Structure |
| 60 | GSA1206 | 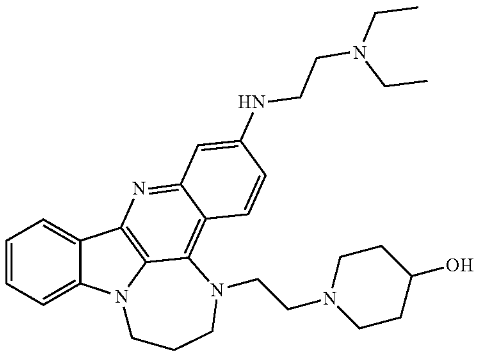 [SMILES: CCN(CC)CCNc1ccc2c3c4c(nc2c1)c1ccccc1n4CCCN3CCN1CCC(O)CC1] |
| 61 | GSA1207 | 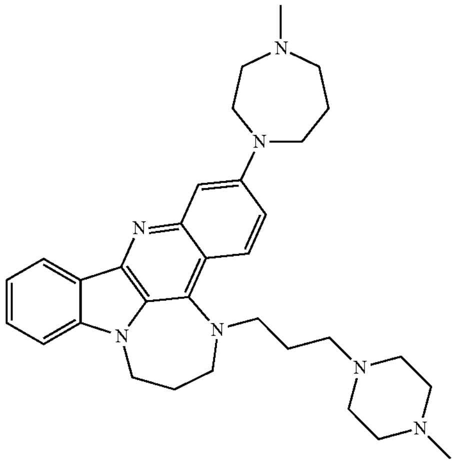 [SMILES: CN1CCN(CCCN2CCCn3c4ccccc4c4nc5cc(N6CCCN(C)CC6)ccc5c2c43)CC1] |
| 62 | GSA1209 | 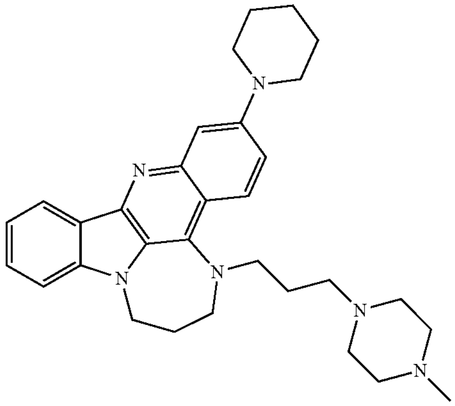 [SMILES: CN1CCN(CCCN2CCCn3c4ccccc4c4nc5cc(N6CCCCC6)ccc5c2c43)CC1] |

TABLE I-continued

Structures of Quindoline compounds

| Compound Number | | Structure |
|---|---|---|
| 63 | GSA1210 | 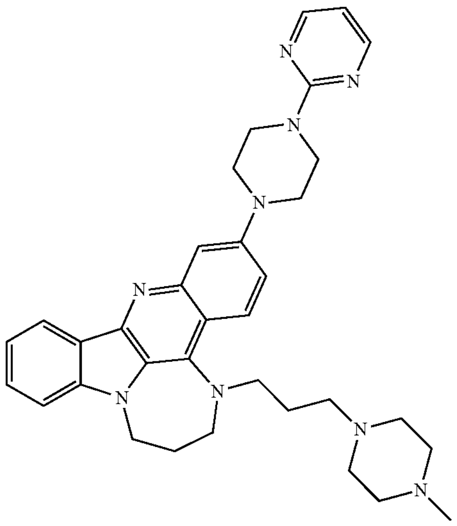 [SMILES: CN1CCN(CCCN2CCCn3c4ccccc4c4nc5cc(N6CCN(c7ncccn7)CC6)ccc5c2c43)CC1] |
| 64 | GSA1211 | 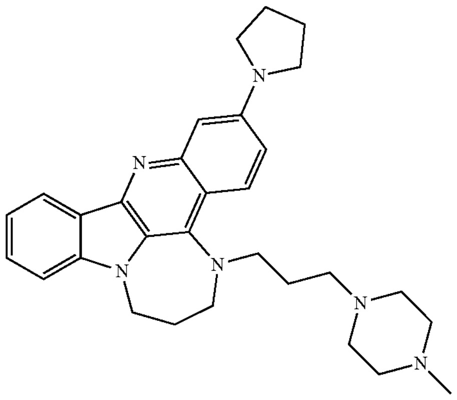 [SMILES: CN1CCN(CCCN2CCCn3c4ccccc4c4nc5cc(N6CCCC6)ccc5c2c43)CC1] |

In some embodiments, the specific quindoline compounds encompassed within Formula II are utilized:

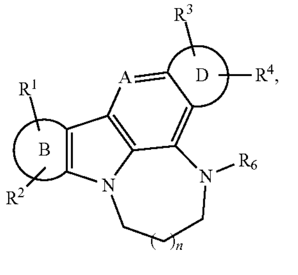

or a pharmaceutically acceptable salt thereof.

Formula II is not limited to a particular chemical structure. In some embodiments, the compound encompassed by Formula II is capable of stabilizing G-quadruplex structures.

In some embodiments, the compound encompassed by Formula II is capable of inhibiting HSV activity and/or expression. In some embodiments, the compound encompassed by Formula II is capable of inhibiting HSV activity and/or expression through stabilization of G-quadruplex structures related to HSV activity and/or expression.

In some embodiments, n is 0, 1, 2, or 3.

In some embodiments, A is —N═ or —$N^+(R^A)$═, wherein $R^A$ is $C_1$-$C_6$alkyl, wherein when A is -$N(R^A)$═, then the compound further comprises a pharmaceutically acceptable anion.

In some embodiments, the B ring and the D ring are each independently a fused phenyl ring or a 6-membered heteroaryl ring comprising one to four annular nitrogen atoms.

In some embodiments, $R^1$, $R^2$, $R^3$ and $R^4$ are each independently hydrogen, $C_1$-$C_6$alkyl, $C_2$-$C_6$alkenyl, $C_2$-$C_6$alkynyl, $C_3$-$C_8$cycloalkyl, heterocyclyl, aryl, heteroaryl, aryl-aryl, aryl-heteroaryl, aryl-heterocyclyl, heteroaryl-aryl, heterocyclyl-aryl, $C_3$-$C_8$cycloalkyl($C_1$-$C_6$)alkyl, heterocyclyl($C_1$-$C_6$)alkyl, aryl($C_1$-$C_6$)alkyl, heteroaryl ($C_1$-$C_6$)alkyl, or $R^{10}$, wherein the alkyl, alkenyl, alkynyl, cycloalkyl, heterocyclyl, aryl, heteroaryl, aryl-aryl, aryl-heteroaryl, aryl-heterocyclyl, heteroaryl-aryl, heterocyclyl-aryl, cycloalkylalkyl, heterocyclylalkyl, arylalkyl, and heteroarylalkyl groups are each optionally substituted by 1, 2, 3, or 4 $R^{10}$ groups, or $R^1$ and $R^2$ are taken together to form a fused phenyl, monocyclic $C_3$-$C_8$cycloalkyl, monocyclic heterocyclyl, monocyclic aryl, or monocyclic heteroaryl ring, each optionally substituted with 1, 2, 3, or 4 $R^{10}$ groups;

or $R^3$ and $R^4$ are taken together to form a fused phenyl, monocyclic $C_3$-$C_8$cycloalkyl, monocyclic heterocyclyl, monocyclic aryl, or monocyclic heteroaryl ring, each optionally substituted with 1, 2, 3, or 4 $R^{10}$ groups.

In some embodiments, each $R^{10}$ is independently $R^{15}$, $C_1$-$C_6$alkyl, —$C_1$-$C_6$alkyl-$R^{15}$.

In some embodiments, each $R^{15}$ is independently halo, nitro, azido, cyano, nitroso, —OR, —SR, —$NR_2$, —C(O)R, —C(O)OR, —C(O)$NR_2$, —S(O)$_2$R, —S(O)$_2NR_2$, —N(R)C(O)R, —N(R)S(O)$_2$R, —OC(O)R, —OC(O)OR, —N(R)C(O)OR, —N(R)C(O)$NR_2$, or —N(R)C(=NR)$NR_2$.

In some embodiments, $R^5$ is $C_1$-$C_6$alkyl, $C_3$-$C_8$cycloalkyl, heterocyclyl, aryl, heteroaryl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl.

In some embodiments, the alkyl, cycloalkyl, heterocyclyl, cycloalkylalkyl, and heterocyclylalkyl groups are optionally substituted with 1, 2, 3, 4, or 5 groups which are each independently oxo, thia, —$R^{50}$, or —$C_1$-$C_6$alkyl-$R^{50}$.

In some embodiments, the aryl, heteroaryl, arylalkyl, and heteroarylalkyl groups are optionally substituted 1, 2, 3, or 4 groups which are each independently $R^{50}$ or —$C_1$-$C_6$alkyl-$R^{50}$.

In some embodiments, each $R^{50}$ is independently halogen, cyano, nitro, azido, nitroso, —OR, —SR, —$NR_2$, —N($R^N$)C(H)($R^{AA}$)C(O)($R^C$), —N(R)$NR_2$, —C(O)R, —C(O)C(H)($R^{AA}$)N(H)($R^N$), —C(O)OR, —C(O)$NR_2$, —C(O)N($R^N$)—C(H)($R^{AA}$)C(O)$R^C$, —C(=NR)$NR_2$, —S(O)$_2$R, —S(O)$_2NR_2$, —N(R)C(O)R, —N(R)C(O)C(H)($R^{AA}$)N(H)($R^N$), —N(R)S(O)$_2$R, —OC(O)R, —OC(O)OR, —N(R)C(O)OR, —N(R)C(O)$NR_2$, —N(R)C(=NR)$NR_2$, $C_1$-$C_6$alkyl, $C_2$-$C_6$alkenyl, $C_2$-$C_6$alkynyl, $C_3$-$C_8$cycloalkyl, heterocyclyl, aryl, or heteroaryl.

In some embodiments, each R is independently hydrogen, $C_1$-$C_6$alkyl, $C_2$-$C_6$alkenyl, $C_2$-$C_6$alkynyl, $C_3$-$C_8$cycloalkyl, heterocyclyl, aryl, heteroaryl, $C_3$-$C_8$cycloalkyl($C_1$-$C_6$)alkyl heterocyclyl($C_1$-$C_6$)alkyl, aryl($C_1$-$C_6$)alkyl, or heteroaryl($C_1$-$C_6$)alkyl, wherein the alkyl, alkenyl, alkynyl, cycloalkyl, heterocyclyl, aryl, heteroaryl, cycloalkylalkyl heterocyclylalkyl, arylalkyl, and heteroarylalkyl are each optionally substituted with 1, 2, 3, or 4 $R^{11}$ groups, or two R groups attached to the same nitrogen atom taken together with the nitrogen atom to which they are attached form a heterocyclyl optionally substituted with 1, 2, 3, or 4 $R^{11}$ groups.

In some embodiments, each $R^{11}$ is independently halo, nitro, azido, cyano, nitroso, —$OR^{12}$, —$SR^{12}$, —N($R^{12}$)$_2$, —C(O)$R^{12}$, —C(O)O$R^{12}$, —C(O)N($R^{12}$)$_2$, —S(O)$_2R^{12}$, —S(O)$_2$N($R^{12}$)$_2$, —N($R^{12}$)C(O)$R^{12}$, —N($R^{12}$)S(O)$_2R^{12}$, —OC(O)$R^{12}$, —OC(O)O$R^{12}$, —N($R^{12}$)C(O)O$R^{12}$, —N($R^{12}$)C(O)N($R^{12}$)$_2$, —N($R^{12}$)C(=N$R^{12}$)N($R^{12}$)$_2$, $C_1$-$C_6$alkyl, $C_2$-$C_6$alkenyl, or $C_2$-$C_6$alkynyl.

In some embodiments, each $R^{12}$ is hydrogen or $C_1$-$C_6$alkyl, or two $R^{12}$ groups attached to the same nitrogen atom taken together with the nitrogen atom to which they are attached form a heterocyclyl optionally substituted with 1 or 2 groups that are each independently halo or $C_1$-$C_6$alkyl.

In some embodiments, each $R^N$ is independently hydrogen or —C(O)C(H)($R^{AA}$)NH($R^{N2}$).

In some embodiments, each $R^C$ is independently —OH or —N($R^{N2}$)C(H)($R^{AA}$)COOH.

In some embodiments, $R^{N2}$ is (i) hydrogen or (ii) $R^{N2}$ and $R^{AA}$ taken together with the atoms to which they are attached form a 4-8 membered heterocyclyl optionally substituted with one or two $R^{A1}$ groups.

In some embodiments, each $R^{AA}$ is hydrogen, $C_1$-$C_6$alkyl, aryl, heteroaryl, aryl$C_1$-$C_6$alkyl, or heteroaryl$C_1$-$C_6$alkyl, wherein the alkyl, arylalkyl, and heteroarylalkyl groups are optionally substituted with 1, 2, 3, 4, or 5 $R^{A1}$ groups, wherein each $R^{A1}$ is independently halo, cyano, —$OR^{A2}$, —$SR^{A2}$, —N($R^{A2}$)$_2$, —C(O)O$R^{A2}$, —C(O)N($R^{A2}$)$_2$, —N($R^{A2}$)C(=N$R^{A2}$)N($R^{A2}$)$_2$, or $C_1$-$C_6$alkyl, wherein each $R^{A2}$ is hydrogen or $C_1$-$C_6$alkyl;

or $R^N$ and $R^{AA}$ taken together with the atoms to which they are attached form a 4-8 membered heterocyclyl optionally substituted with one or two $R^{A1}$ groups.

Such methods and uses further contemplate the use of a subgenera of compounds encompassed within Formula II in which the substituents are selected as any and all combinations of structural formula II, A, $R^1$-$R^4$, and $R^5$ as defined herein, including without limitation, the following:

(IIa)

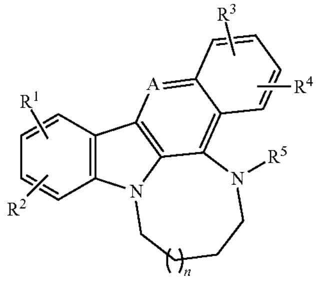

(IIb)

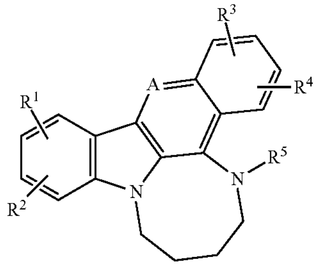

(IIc)

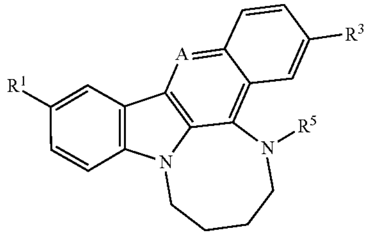

(IId)

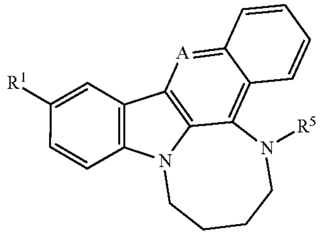

or

-continued (IIe)

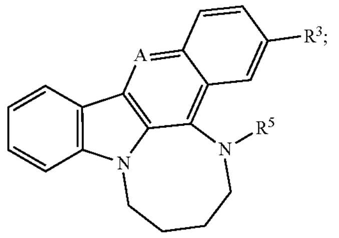

wherein, when present, each B is independently —N— or —C(H)—, and wherein when B is —C(H)—, then B can be optionally substituted with $R^1$, $R^2$, $R^3$, or $R^4$ when the ring in which each B is present is allowed to be substituted by $R^1$-$R^4$ as defined in the preceding formulae.

In some embodiments, A is selected from one of the following groups (a)-(c):

(a) A is —N═.

(b) A is —N($R^A$)═, wherein $R^A$ is $C_1$-$C_6$alkyl, and wherein the compound further comprises a pharmaceutically acceptable anion.

(c) A is —N($R^A$)═, and the pharmaceutically acceptable anion is a halide.

In some embodiments, $R^1$-$R^4$ are selected from one of the following groups (d)-(ss):

(d) One of $R^1$, $R^2$, $R^3$ and $R^4$ is —$OR^{16}$, —$SR^{16}$, or —N(H)($R^{16}$), wherein $R^{16}$ is $C_1$-$C_6$alkyl, or —$C_1$-$C_6$alkyl-$R^{17}$, heterocyclyl($C_1$-$C_6$)alkyl, aryl($C_1$-$C_6$)alkyl, or heteroaryl($C_1$-$C_6$)alkyl, wherein $R^{17}$ is —$OR^{18}$, —$SR^{18}$, —N($R^{18}$)$_2$, —C(O)$R^{18}$, —C(O)O$R^{18}$, —C(O)N($R^{18}$)$_2$, —S(O)$_2R^{18}$, —S(O)$_2$N($R^{18}$)$_2$, —N($R^{18}$)C(O)$R^{18}$, —N($R^{18}$)S(O)$_2R^{18}$, —OC(O)$R^{18}$, —OC(O)O$R^{18}$, —N($R^{18}$)C(O)O$R^{18}$, —N($R^{18}$)C(O)N($R^{18}$)$_2$, or —N($R^{18}$)C(═N$R^{18}$)N($R^{18}$)$_2$, wherein each $R^{18}$ is hydrogen or $C_1$-$C_6$alkyl.

(e) $R^2$ and $R^4$ are each hydrogen; and $R^1$ and $R^3$ are each independently —$OR^{16}$, —$SR^{16}$, or —N(H)($R^{16}$), wherein $R^{16}$ is $C_1$-$C_6$alkyl, or —$C_1$-$C_6$alkyl-$R^{17}$, heterocyclyl($C_1$-$C_6$)alkyl, aryl($C_1$-$C_6$)alkyl, or heteroaryl($C_1$-$C_6$)alkyl, wherein $R^{17}$ is —$OR^{18}$, —$SR^{18}$, —N($R^{18}$)$_2$, —C(O)$R^{18}$, —C(O)O$R^{18}$, —C(O)N($R^{18}$)$_2$, —S(O)$_2R^{18}$, —S(O)$_2$N($R^{18}$)$_2$, —N($R^{18}$)C(O)$R^{18}$, —N($R^{18}$)S(O)$_2R^{18}$, —OC(O)$R^{18}$, —OC(O)O$R^{18}$, —N($R^{18}$)C(O)O$R^{18}$, —N($R^{18}$)C(O)N($R^{18}$)$_2$, or —N($R^{18}$)C(═N$R^{18}$)N($R^{18}$)$_2$, wherein each $R^{18}$ is hydrogen or $C_1$-$C_6$alkyl.

(f) $R^2$ and $R^4$ are each hydrogen; one of $R^1$ and $R^3$ is —$OR^{16}$, —$SR^{16}$, or —N(H)($R^{16}$), wherein $R^{16}$ is $C_1$-$C_6$alkyl, or —$C_1$-$C_6$alkyl-$R^{17}$, heterocyclyl($C_1$-$C_6$)alkyl, aryl($C_1$-$C_6$)alkyl, or heteroaryl($C_1$-$C_6$)alkyl, wherein $R^{17}$ is —$OR^{18}$, —$SR^{18}$, —N($R^{18}$)$_2$, —C(O)$R^{18}$, —C(O)O$R^{18}$, —C(O)N($R^{18}$)$_2$, —S(O)$_2R^{18}$, —S(O)$_2$N($R^{18}$)$_2$, —N($R^{18}$)C(O)$R^{18}$, —N($R^{18}$)S(O)$_2R^{18}$, —OC(O)$R^{18}$, —OC(O)O$R^{18}$, —N($R^{18}$)C(O)O$R^{18}$, —N($R^{18}$)C(O)N($R^{18}$)$_2$, or —N($R^{18}$)C(═N$R^{18}$)N($R^{18}$)$_2$, wherein each $R^{18}$ is hydrogen or $C_1$-$C_6$alkyl; and the other of $R^1$ and $R^3$ is hydrogen.

(g) Group (f), wherein $R^1$ is hydrogen.

(h) Group (f), wherein $R^3$ is hydrogen.

(i) $R^2$ and $R^4$ are each hydrogen; and $R^1$ and $R^3$ are each independently —N(H)$R^{16}$, wherein $R^{16}$ is $C_1$-$C_6$alkyl, or —$C_1$-$C_6$alkyl-$R^{17}$, heterocyclyl($C_1$-$C_6$)alkyl, aryl($C_1$-$C_6$)alkyl, or heteroaryl($C_1$-$C_6$)alkyl, wherein $R^{17}$ is —$OR^{18}$, —$SR^{18}$, —N($R^{18}$)$_2$, —C(O)$R^{18}$, —C(O)O$R^{18}$, —C(O)N($R^{18}$)$_2$, —S(O)$_2R^{18}$, —S(O)$_2$N($R^{18}$)$_2$, —N($R^{18}$)C(O)$R^{18}$, —N($R^{18}$)S(O)$_2R^{18}$, —OC(O)$R^{18}$, —OC(O)O$R^{18}$, —N($R^{18}$)C(O)O$R^{18}$, —N($R^{18}$)C(O)N($R^{18}$)$_2$, or —N($R^{18}$)C(═N$R^{18}$)N($R^{18}$)$_2$, wherein each $R^{18}$ is hydrogen or $C_1$-$C_6$alkyl.

(j) $R^2$ and $R^4$ are each hydrogen; one of $R^1$ and $R^3$ is —N(H)$R^{16}$, wherein $R^{16}$ is $C_1$-$C_6$alkyl, or —$C_1$-$C_6$alkyl-$R^{17}$, heterocyclyl($C_1$-$C_6$)alkyl, aryl($C_1$-$C_6$)alkyl, or heteroaryl($C_1$-$C_6$)alkyl, wherein $R^{17}$ is —$OR^{18}$, —$SR^{18}$, —N($R^{18}$)$_2$, —C(O)$R^{18}$, —C(O)O$R^{18}$, —C(O)N($R^{18}$)$_2$, —S(O)$_2R^{18}$, —S(O)$_2$N($R^{18}$)$_2$, —N($R^{18}$)C(O)$R^{18}$, —N($R^{18}$)S(O)$_2R^{18}$, —OC(O)$R^{18}$, —OC(O)O$R^{18}$, —N($R^{18}$)C(O)O$R^{18}$, —N($R^{18}$)C(O)N($R^{18}$)$_2$, or —N($R^{18}$)C(═N$R^{18}$)N($R^{18}$)$_2$, wherein each $R^{18}$ is hydrogen or $C_1$-$C_6$alkyl; and the other of $R^1$ and $R^3$ is hydrogen.

(k) Group (j), wherein $R^1$ is hydrogen.

(l) Group (j), wherein $R^3$ is hydrogen.

(m) $R^2$ and $R^4$ are each hydrogen; and $R^1$ and $R^3$ are each independently —N(H)$R^{16}$, wherein $R^{16}$ is —$C_1$-$C_6$alkyl-$R^{17}$ or heterocyclyl($C_1$-$C_6$)alkyl, wherein $R^{17}$ is —$OR^{18}$, —$SR^{18}$, —N($R^{18}$)$_2$, —N($R^{18}$)C(O)$R^{18}$, —N($R^{18}$)S(O)$_2R^{18}$, —OC(O)$R^{18}$, —OC(O)O$R^{18}$, —N($R^{18}$)C(O)O$R^{18}$, —N($R^{18}$)C(O)N($R^{18}$)$_2$, or —N($R^{18}$)C(═N$R^{18}$)N($R^{18}$)$_2$, wherein each $R^{18}$ is hydrogen or $C_1$-$C_6$alkyl.

(n) $R^2$ and $R^4$ are each hydrogen; one of $R^1$ and $R^3$ is —N(H)$R^{16}$, wherein $R^{16}$ is —$C_1$-$C_6$alkyl-$R^{17}$ or heterocyclyl($C_1$-$C_6$)alkyl, wherein $R^{17}$ is —$OR^{18}$, —$SR^{18}$, —N($R^{18}$)$_2$, —N($R^{18}$)C(O)$R^{18}$, —N($R^{18}$)S(O)$_2R^{18}$, —OC(O)$R^{18}$, —OC(O)O$R^{18}$, —N($R^{18}$)C(O)O$R^{18}$, —N($R^{18}$)C(O)N($R^{18}$)$_2$, or —N($R^{18}$)C(═N$R^{18}$)N($R^{18}$)$_2$, wherein each $R^{18}$ is hydrogen or $C_1$-$C_6$alkyl, and the other of $R^1$ and $R^3$ is hydrogen.

(o) Group (n), wherein $R^1$ is hydrogen.

(p) Group (n), wherein $R^3$ is hydrogen.

(q) One of $R^1$, $R^2$, $R^3$ and $R^4$ is heterocyclyl, aryl, or heteroaryl, wherein the heterocyclyl, aryl, and heteroaryl groups are each optionally substituted by a one group which is $R^{20}$, $C_1$-$C_6$alkyl, or —$C_1$-$C_6$alkyl-$R^{20}$, wherein $R^{20}$ is —$OR^{21}$, —$SR^{21}$, —N($R^{21}$)$_2$, —C(O)$R^{21}$, —C(O)O$R^{21}$, —C(O)N($R^{21}$)$_2$, —S(O)$_2R^{21}$, —S(O)$_2$N($R^{21}$)$_2$, —N($R^{21}$)C(O)$R^{21}$, —N($R^{21}$)S(O)$_2R^{21}$, —OC(O)$R^{21}$, —OC(O)O$R^{21}$, —N($R^{21}$)C(O)O$R^{21}$, —N($R^{21}$)C(O)N($R^{21}$)$_2$, or —N($R^{21}$)C(═N$R^{21}$)N($R^{21}$)$_2$, wherein each $R^{21}$ is independently hydrogen; $C_1$-$C_6$alkyl; or heterocyclyl optionally substituted with 1, 2, 3, or 4 $R^{11}$ groups.

(r) Group (q), wherein $R^2$ and $R^4$ are hydrogen.

(s) Group (q), wherein $R^1$, $R^2$, and $R^4$ are hydrogen.

(t) Group (q), wherein $R^2$, $R^3$, and $R^4$ are hydrogen.

(u) One of $R^1$, $R^2$, $R^3$ and $R^4$ is heterocyclyl, aryl, or heteroaryl, wherein the heterocyclyl, aryl, and heteroaryl groups are each optionally substituted by a one group which is $R^{20}$, $C_1$-$C_6$alkyl, or —$C_1$-$C_6$alkyl-$R^{20}$, wherein $R^{20}$ is —$OR^{21}$, —$SR^{21}$, —N($R^{21}$, —C(O)$R^{21}$, —C(O)$R^{21}$, —C(O)O$R^{21}$, —C(O)N($R^{21}$)$_2$, —S(O)$_2R^{21}$, —S(O)$_2$N($R^{21}$)$_2$, wherein each $R^{21}$ is independently hydrogen; $C_1$-$C_6$alkyl; or heterocyclyl optionally substituted with 1, 2, 3, or 4 $R^{11}$ groups.

(v) Group (u), wherein $R^2$ and $R^4$ are hydrogen.

(w) Group (u), wherein $R^1$, $R^2$, and $R^4$ are hydrogen.

(x) Group (u), wherein $R^2$, $R^3$, and $R^4$ are hydrogen.

(y) At least one of $R^1$, $R^2$, $R^3$ and $R^4$ is

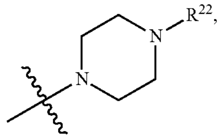

wherein $R^{22}$ is —C(O)$R^{21}$, —C(O)O$R^{21}$, —C(O)N($R^{21}$)$_2$, —S(O)$_2$$R^{21}$, —S(O)$_2$N($R^{21}$)$_2$, $C_1$-$C_6$alkyl, or —$C_1$-$C_6$alkyl-$R^{20}$, wherein $R^{20}$ is —O$R^{21}$, —S$R^{21}$, —N($R^{21}$)$_2$, —C(O)$R^{21}$, —C(O)O$R^{21}$, —C(O)N($R^{21}$)$_2$, —S(O)$_2$$R^{21}$, —S(O)$_2$N($R^{21}$)$_2$, and each $R^{21}$ is independently hydrogen; $C_1$-$C_6$alkyl; or heterocyclyl optionally substituted with 1, 2, 3, or 4 $R^{11}$ groups.

(z) Group (y), wherein $R^1$ and $R^3$ are each independently

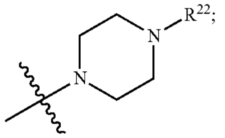

and $R^2$ and $R^4$ are hydrogen.

(aa) Group (y), wherein $R^1$, $R^2$, and $R^4$ are hydrogen.

(bb) Group (y), wherein $R^2$, $R^3$, and $R^4$ are hydrogen.

(cc) At least one of $R^1$, $R^2$, $R^3$ and $R^4$ is

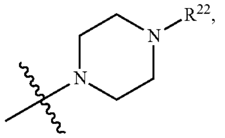

wherein $R^{22}$ is $C_1$-$C_6$alkyl, or —$C_1$-$C_6$alkyl-$R^{20}$ wherein $R^{20}$ is —O$R^{21}$, —S$R^{21}$, —N($R^{21}$)$_2$, —N($R^{21}$)C(O)$R^{21}$, —N($R^{21}$)S(O)$_2$$R^{21}$, —OC(O)$R^{21}$, —OC(O)O$R^{21}$, —N($R^{21}$)C(O)O$R^{21}$, —N($R^{21}$)C(O)N($R^{21}$)$_2$, or —N($R^{21}$)C(=N$R^{21}$)N($R^{21}$)$_2$, wherein each $R^{21}$ is independently hydrogen; $C_1$-$C_6$alkyl; or heterocyclyl optionally substituted with 1, 2, 3, or 4 $R^{11}$ groups.

(dd) Group (cc), wherein $R^1$ and $R^3$ are each independently

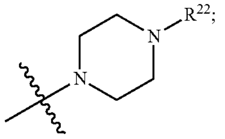

and $R^2$ and R4 are hydrogen.

(ee) Group (cc), wherein $R^1$, $R^2$, and $R^4$ are hydrogen.

(ff) Group (cc), wherein $R^2$, $R^3$, and $R^4$ are hydrogen.

(gg) At least one of $R^1$, $R^2$, $R^3$ and $R^4$ is

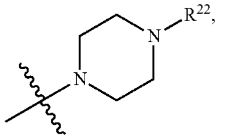

wherein $R^{22}$ is $C_1$-$C_6$alkyl, or —$C_1$-$C_6$alkyl-$R^{20}$, wherein $R^{20}$ is —O$R^{21}$, —S$R^{21}$, or —N($R^{21}$)$_2$, wherein each $R^{21}$ is independently hydrogen; $C_1$-$C_6$alkyl; or heterocyclyl optionally substituted with 1, 2, 3, or 4 $R^{11}$ groups.

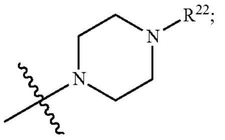

(hh) Group (gg), wherein $R^1$ and $R^3$ are each independently and $R^2$ and $R^4$ are hydrogen.

(ii) Group (gg), wherein $R^1$, $R^2$, and $R^4$ are hydrogen.

(jj) Group (gg), wherein $R^2$, $R^3$, and $R^4$ are hydrogen.

(kk) At least one of $R^1$, $R^2$, $R^3$ and $R^4$ is

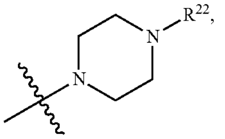

wherein $R^{22}$ is —C(O)$R^{21}$ or —S(O)$_2$$R^{21}$ each $R^{21}$ is independently hydrogen; $C_1$-$C_6$alkyl; or heterocyclyl optionally substituted with 1, 2, 3, or 4 $R^{11}$ groups.

(ll) Group (kk), wherein $R^1$ and $R^3$ are each independently

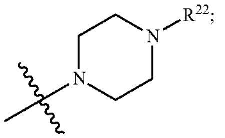

and $R^2$ and $R^4$ are hydrogen.

(mm) Group (kk), wherein $R^1$, $R^2$, and $R^4$ are hydrogen.

(nn) Group (kk), wherein $R^2$, $R^3$, and $R^4$ are hydrogen.

(oo) Any one of groups q-(nn), wherein each $R^{21}$ is independently hydrogen or $C_1$-$C_6$alkyl.

(pp) At least one of $R^1$, $R^2$, $R^3$ and $R^4$ is

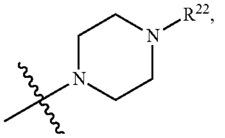

wherein $R^{22}$ is —C(O)$R^{21}$ or —S(O)$_2$$R^{21}$, wherein $R^{21}$ is heterocyclyl optionally substituted with 1, 2, 3, or 4 $R^{11}$ groups.

(qq) Group (pp), wherein $R^1$ and $R^3$ are each independently

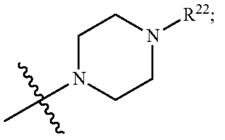

and $R^2$ and $R^4$ are hydrogen.

(rr) Group (pp), wherein $R^1$, $R^2$, and $R^4$ are hydrogen.

(ss) Group (pp), wherein $R^2$, $R^3$, and $R^4$ are hydrogen.

In some embodiments, $R^5$ is selected from one of the following groups (tt)-(zzz):

(tt) $R^5$ is —$C_1$-$C_6$alkyl-$R^{50}$, wherein $R^{50}$ is —OR, —SR, —$NR_2$, —N(R)C(H)($R^{AA}$)C(O)($R^C$), —N(R)$NR_2$, —N(R)C(O)R, —N(R)C(O)C(H)($R^{AA}$)N(H)($R^N$), —N(R)S(O)$_2$R, —OC(O)R, —OC(O)OR, —N(R)C(O)OR, —N(R)C(O)$NR_2$, or —N(R)C(=NR)$NR_2$.

(uu) $R^5$ is —$C_1$-$C_6$alkyl-$R^{50}$, wherein $R^{50}$ is —N(H)C(O)$R^{53}$, —N(H)S(O)$_2R^{53}$, —OC(O)$R^{53}$, —OC(O)O$R^{53}$, —N(H)C(O)O$R^{53}$, —N(H)C(O)N(H)$R^{53}$, wherein $R^{53}$ is $C_1$-$C_6$alkyl, $C_3$-$C_8$cycloalkyl, heterocyclyl, aryl, or heteroaryl, each optionally substituted with 1 or 2 $R^{11}$ groups.

(vv) $R^5$ is —$C_1$-$C_6$alkyl-$R^{50}$, wherein $R^{50}$ is —N(H)C(O)$R^{53}$, —N(H)S(O)$_2R^{53}$, —OC(O)$R^{53}$, —OC(O)O$R^{53}$, —N(H)C(O)O$R^{53}$, —N(H)C(O)N(H)$R^{53}$, wherein $R^{53}$ is $C_1$-$C_6$alkyl, $C_3$-$C_8$cycloalkyl, heterocyclyl, aryl, or heteroaryl.

(ww) Group (uu), wherein $R^{53}$ is $C_1$-$C_6$alkyl, $C_3$-$C_8$cycloalkyl, heterocyclyl, aryl, or heteroaryl, each optionally substituted with 1 or 2 groups which are each independently halo, —O$R^{12}$, —S$R^{12}$, —N($R^{12}$)$_2$, or $C_1$-$C_6$alkyl, wherein each $R^{12}$ is hydrogen or $C_1$-$C_6$alkyl.

(xx) Group (uu), wherein $R^{53}$ is heterocyclyl optionally substituted with 1 or 2 groups which are each independently halo, —O$R^{12}$, —S$R^{12}$, —N($R^{12}$)$_2$, or $C_1$-$C_6$alkyl, wherein each $R^{12}$ is hydrogen or $C_1$-$C_6$alkyl.

(yy) Group (uu), wherein $R^{53}$ is pyrrolidinyl, tetrahydrofuranyl, tetrahydrothienyl, imidazolidinyl, oxazolidinyl, thiazolidinyl, piperidinyl, piperazinyl, morpholinyl, thiomorpholinyl, azepanyl, diazepanyl, pyrrolinyl, imidazolinyl, oxazolinyl, or thiazolinyl, each optionally substituted with 1 or 2 groups which are each independently halo, —O$R^{12}$, —S$R^{12}$)$_2$, —N($R^{12}$)$_2$, or $C_1$-$C_6$alkyl, wherein each $R^{12}$ is hydrogen or $C_1$-$C_6$alkyl.

(zz) Group (uu), wherein $R^{53}$ is pyrrolidinyl, imidazolidinyl, piperidinyl, piperazinyl, azepanyl, or diazepanyl, each optionally substituted with 1 or 2 groups which are each independently halo, —O$R^{12}$, —S$R^{12}$, —N($R^{12}$)$_2$, or $C_1$-$C_6$alkyl, wherein each $R^{12}$ is hydrogen or $C_1$-$C_6$alkyl.

(aaa) $R^5$ is heterocyclyl($C_1$-$C_6$)alkyl optionally substituted with 1, 2, 3, 4, or 5 groups which are each independently oxo, thia, or —$R^{50}$.

(bbb) $R^5$ is heterocyclyl($C_1$-$C_6$)alkyl optionally substituted with 1, 2, or 3 groups which are each independently oxo, thia, or —$R^{50}$.

(ccc) $R^5$ is of the formula,

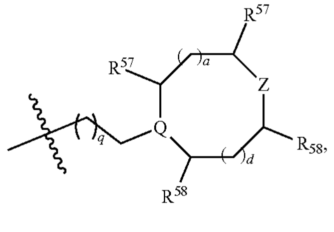

wherein a and d are each independently 0, 1, or 2;

q is 0, 1, 2, 3, 4 or 5;

Q is —N— or —C(H)—;

Z is a bond, —O—, —S—, —C(O)—, or —N($R^{60}$)—, wherein $R^{60}$ is hydrogen, $C_1$-$C_6$alkyl, aryl, heteroaryl, heterocyclyl, $C_3$-$C_8$cycloalkyl, aryl($C_1$-$C_6$)alkyl, heteroaryl($C_1$-$C_6$)alkyl, heterocyclyl($C_1$-$C_6$)alkyl, $C_3$-$C_8$cycloalkyl($C_1$-$C_6$)alkyl, —$C_1$-$C_6$alkyl-OR, —$C_1$-$C_6$alkyl-SR, —$C_1$-$C_6$alkyl-N(R)$_2$, —COR, —$CONR_2$, —C(O)C(H)($R^{AA}$)N(H)($R^N$), —C(=NR)$NR_2$, —$SO_2$R, —COOR; and each $R^{57}$ and $R^{58}$ are independently hydrogen, $C_1$-$C_6$alkyl, aryl, heteroaryl, heterocyclyl, $C_3$-$C_8$cycloalkyl, —OR, —$NR_2$, —N(R)C(O)$NR_2$, oxo, —COOH, —$CONR_2$, —C(O)C(H)($R^{AA}$)N(H)($R^N$), or —N(R)C(H)($R^{AA}$)C(O)($R^C$), or when a is 0, then both $R^{57}$ groups can be taken together with the carbon atoms to which they are attached form a fused aryl, heteroaryl, heterocyclyl, or $C_3$-$C_8$cycloalkyl, wherein the fused aryl and heteroaryl groups are each optionally substituted with 1 or 2 $R^{50}$ groups; and wherein the fused heterocyclyl and cycloalkyl groups are each optionally substituted with 1 or 2 oxo, thia, or $R^{50}$ groups;

or when d is 0, both $R^{58}$ groups can be taken together with the carbon atoms to which they are attached form a fused aryl, heteroaryl, heterocyclyl, or $C_3$-$C_8$cycloalkyl, wherein the fused aryl and heteroaryl groups are each optionally substituted with 1 or 2 $R^{50}$ groups; and wherein the fused heterocyclyl and cycloalkyl groups are each optionally substituted with 1 or 2 oxo, thia, or $R^{50}$ groups.

(ddd) Group (ccc) wherein Q is —N—.

(eee) Group (ccc), wherein Q is —N—; and a is 0.

(fff) Group (ccc), wherein Q is —N—; and a and d are each 0.

(ggg) Group (ccc), wherein Q is —N— and Z is a bond or —O—.

(hhh) Group (ccc) wherein Q is —N—; a is 0; and both $R^{57}$ groups taken together with the carbon atoms to which they are attached form a fused aryl, heteroaryl, heterocyclyl, or $C_3$-$C_8$cycloalkyl, wherein the fused aryl and heteroaryl groups are each optionally substituted with 1 or 2 $R^{50}$ groups; and wherein the fused heterocyclyl and cycloalkyl groups are each optionally substituted with 1 or 2 oxo, thia, or $R^{50}$ groups; and each $R^{58}$ is independently hydrogen, $C_1$-$C_6$alkyl, aryl, heteroaryl, heterocyclyl, $C_3$-$C_8$cycloalkyl, —OR, —$NR_2$, —N(R)C(O)$NR_2$, oxo, —COOH, —$CONR_2$, —C(O)C(H)($R^{AA}$)N(H)($R^N$), or —N(R)C(H)($R^{AA}$)C(O)($R^C$).

(iii) Group (hhh), wherein each $R^{58}$ is independently hydrogen.

(jjj) Group (hhh), wherein both $R^{57}$ groups taken together with the carbon atoms to which they are attached form a fused phenyl, 5 or 6-membered monocyclic heteroaryl, 5 or 6 membered monocyclic heterocyclyl, or a $C_5$-$C_6$cycloalkyl, wherein the fused phenyl and heteroaryl groups are each optionally substituted with 1 or 2 $R^{50}$ groups; and wherein the fused heterocyclyl and cycloalkyl groups are each optionally substituted with 1 or 2 oxo, thia, or $R^{50}$ groups.

(kkk) Group (hhh), wherein d is 0 and both $R^{58}$ groups taken together with the carbon atoms to which they are attached form a fused aryl, heteroaryl, heterocyclyl, or $C_3$-$C_8$cycloalkyl, wherein the fused aryl and heteroaryl groups are each optionally substituted with 1 or 2 $R^{50}$ groups; and wherein the fused heterocyclyl and cycloalkyl groups are each optionally substituted with 1 or 2 oxo, thia, or $R^{50}$ groups.

(lll) Group (kkk), wherein both $R^{57}$ groups taken together with the carbon atoms to which they are attached and both $R^{58}$ groups taken together with the carbon atoms to which they are attached independently form a fused phenyl, 5 or 6-membered monocyclic heteroaryl, 5 or 6 membered monocyclic heterocyclyl, or $C_5$-$C_6$cycloalkyl, wherein the fused phenyl and heteroaryl groups are each optionally substituted with 1 or 2 $R^{50}$ groups; and wherein the fused heterocyclyl and cycloalkyl groups are each optionally substituted with 1 or 2 oxo, thia, or $R^{50}$ groups.

(mmm) Group (kkk), wherein both $R^{57}$ groups taken together with the carbon atoms to which they are attached and both $R^{58}$ groups taken together with the carbon atoms to which they are attached independently form a fused phenyl, 5 or 6-membered monocyclic heteroaryl, 5 or 6 membered monocyclic heterocyclyl, or $C_5$-$C_6$cycloalkyl, wherein the fused phenyl and heteroaryl groups are each optionally substituted with 1 or 2 $R^{70}$ groups; and wherein the fused heterocyclyl and cycloalkyl groups are each optionally substituted with 1 or 2 oxo, thia, or $R^{70}$ groups, wherein each $R^{70}$ is independently halogen, $C_1$-$C_6$alkyl, —$OR^{65}$, —$SR^{65}$, —$N(R^{65})_2$, —$C(O)R^{65}$, —$C(O)OR^{65}$, —$C(O)N(R^{65})_2$, —$S(O)_2R^{65}$, —$S(O)_2N(R^{65})_2$, —$N(R^{65})C(O)R^{65}$, —$N(R^{65})S(O)_2R^{65}$, —$OC(O)R^{65}$, —$OC(O)OR^{65}$, —$N(R)C(O)OR^{65}$, —$N(R^{65})C(O)N(R^{65})_2$, wherein each $R^{65}$ is independently hydrogen or $C_1$-$C_6$ alkyl.

(ooo) $R^5$ is —$(CH_2)_{1-6}$-$R^{61}$, wherein $R^{61}$ is a group which is

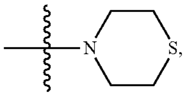 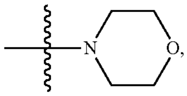

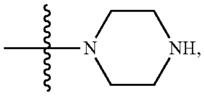 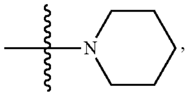

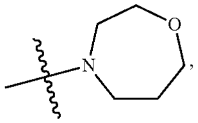 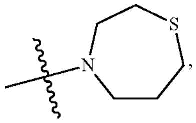 or

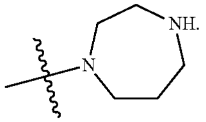

(ppp) $R^5$ is —$(CH_2)_{1-6}$—$R^{61}$, wherein $R^{61}$ is a group which is

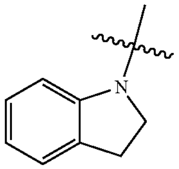 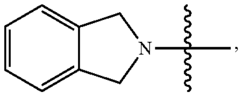

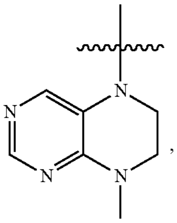 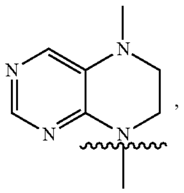

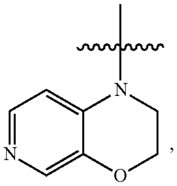 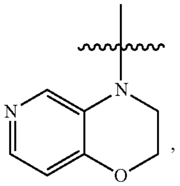

-continued

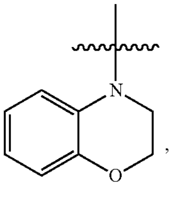 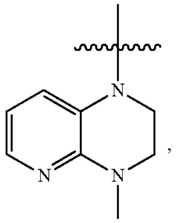

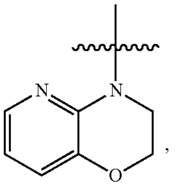 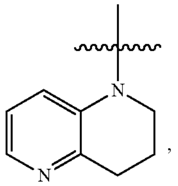

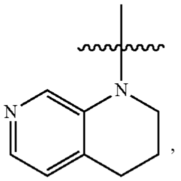 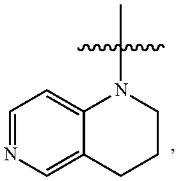

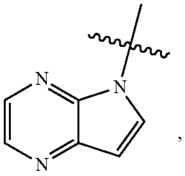 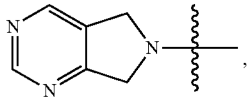

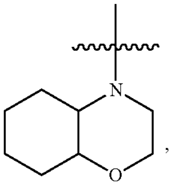 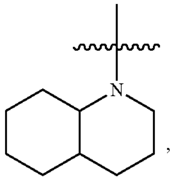

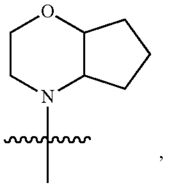 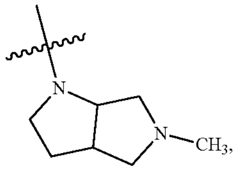

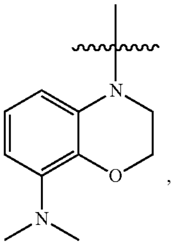 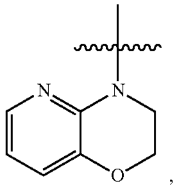

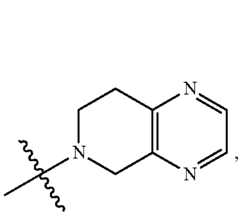 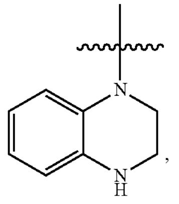

-continued

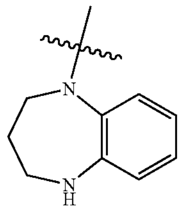
,
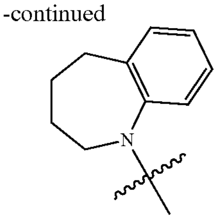
, or

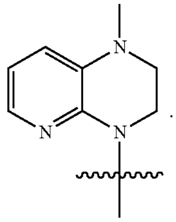
.

(rrr) $R^5$ is —$(CH_2)_m$—N(H)$R^{56}$, wherein m is 2, 3, 4, 5, or 6, and $R^{56}$ is aryl or heteroaryl, each optionally substituted with 1, 2, 3, or 4 groups which are each independently $R^{50}$.

(sss) $R^5$ is —$(CH_2)_m$—N(H)$R^{56}$, wherein m is 2, 3, 4, 5, or 6, and $R^{56}$ is phenyl or a mono or bicyclic heteroaryl, each optionally substituted with 1, 2, 3, or 4 groups which are each independently $R^{50}$.

(ttt) $R^5$ is —$(CH_2)_m$—N(H)$R^{56}$, wherein m is 2, 3, 4, 5, or 6, and $R^{56}$ is phenyl optionally substituted with 1, 2, 3, or 4 groups which are each independently $R^{50}$.

(uuu) $R^5$ is —$(CH_2)_m$—N(H)$R^{56}$, wherein m is 2, 3, 4, 5, or 6, and $R^{56}$ is a mono or bicyclic heteroaryl, each optionally substituted with 1, 2, 3, or 4 groups which are each independently $R^{50}$.

(vvv) $R^5$ is —$(CH_2)_m$—N(H)$R^{56}$, wherein m is 2 or 3, and $R^{56}$ is aryl or heteroaryl, each optionally substituted with 1, 2, 3, or 4 groups which are each independently $R^{50}$.

(www) $R^5$ is —$(CH_2)_m$—N(H)$R^{56}$, wherein m is 2 or 3, and $R^{56}$ is phenyl or a mono or bicyclic heteroaryl, each optionally substituted with 1, 2, 3, or 4 groups which are each independently $R^{50}$.

(xxx) $R^5$ is —$(CH_2)_m$—N(H)$R^{56}$, wherein m is 2 or 3, and $R^{56}$ is phenyl optionally substituted with 1, 2, 3, or 4 groups which are each independently $R^{50}$.

(yyy) $R^5$ is —$(CH_2)_m$—N(H)$R^{56}$, wherein m is 2 or 3, and $R^{56}$ is a mono or bicyclic heteroaryl, each optionally substituted with 1, 2, 3, or 4 groups which are each independently $R^{50}$.

(zzz) $R^5$ is —$(CH_2)_m$—N(H)$R^{56}$, wherein m is 2, 3, 4, 5, or 6, and $R^{56}$ is

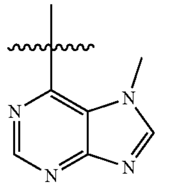
or
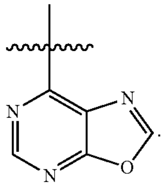
.

In some embodiments, compounds encompassed within Formula II are provided, wherein A is —N═ or —N($R^A$)═, wherein $R^A$ is $C_1$-$C_6$alkyl, wherein when A is —N($R^A$)═, then the compound further comprises a pharmaceutically acceptable anion;

the B ring and the D ring are each independently a fused phenyl ring;

$R^1$, $R^2$, $R^3$ and $R^4$ are each independently hydrogen, $C_1$-$C_6$alkyl, $C_3$-$C_8$cycloalkyl, heterocyclyl, aryl, heteroaryl, or $R^{10}$, wherein the alkyl, cycloalkyl, heterocyclyl, aryl, and heteroaryl groups are each optionally substituted by 1 or 2 $R^{10}$ groups, wherein each $R^{10}$ is independently $R^{15}$, $C_1$-$C_6$alkyl, —$C_1$-$C_6$alkyl-$R^{15}$, wherein each $R^{15}$ is independently halo, nitro, azido, cyano, nitroso, —OR, —SR, —$NR_2$, —C(O)R, —C(O)OR, —C(O)$NR_2$, —S$(O)_2$R, —S$(O)_2NR_2$, —N(R)C(O)R, —N(R)S$(O)_2$R, —OC(O)R, —OC(O)OR, —N(R)C(O)OR, —N(R)C(O)$NR_2$, or —N(R)C(═NR)$NR_2$; and $R^5$ is $C_1$-$C_6$alkyl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl, wherein the alkyl, cycloalkylalkyl, and heterocyclylalkyl groups are optionally substituted with 1 or 2 groups which are each independently oxo or —$R^{50}$; and the arylalkyl and heteroarylalkyl groups are optionally substituted 1, 2, 3, or 4 groups which are each independently —$R^{50}$ or —$C_1$-$C_6$alkyl-$R^{50}$, wherein each $R^{50}$ is independently halogen, cyano, nitro, azido, nitroso, —OR, —SR, —$NR_2$, —N(R)C(H)($R^{AA}$)C(O)($R^C$), —N(R)$NR_2$, —C(O)R, —C(O)C(H)($R^{AA}$)N(H)($R^N$), —C(O)OR, —C(O)$NR_2$, —C(O)N(R)—C(H)($R^{AA}$)C(O)$R^C$, —C(═NR)$NR_2$, —S$(O)_2$R, —S$(O)_2$ $NR_2$, —N(R)C(O)R, —N(R)C(O)C(H)($R^{AA}$)N(H)($R^N$), —N(R)S$(O)_2$R, —OC(O)R, —OC(O)OR, —N(R)C(O)OR, —N(R)C(O)$NR_2$, —N(R)C(═NR)$NR_2$, or $C_1$-$C_6$alkyl, wherein each R is independently hydrogen, $C_1$-$C_6$alkyl, $C_2$-$C_6$alkenyl, $C_2$-$C_6$alkynyl, $C_3$-$C_8$cycloalkyl, heterocyclyl, aryl, heteroaryl, $C_3$-$C_8$cycloalkyl($C_1$-$C_6$)alkyl heterocyclyl($C_1$-$C_6$)alkyl, aryl($C_1$-$C_6$)alkyl, or heteroaryl($C_1$-$C_6$)alkyl, wherein the alkyl, alkenyl, alkynyl, cycloalkyl, heterocyclyl, aryl, heteroaryl, cycloalkylalkyl heterocyclylalkyl, arylalkyl, and heteroarylalkyl are each optionally substituted with 1 or 2 $R^{11}$ groups, wherein each $R^{11}$ is independently halo, nitro, azido, cyano, nitroso, —$OR^{12}$, —$SR^{12}$, —N$(R^{12})_2$, —C(O)$R^{12}$, —C(O)$OR^{12}$, —C(O)N$(R^{12})_2$, —S$(O)_2R^{12}$, —S$(O)_2$N$(R^{12})_2$, —N($R^{12}$)C(O)$R^{12}$, —N($R^{12}$)S$(O)_2$ $R^{12}$, —OC(O)$R^{12}$, —OC(O)$OR^{12}$, —N($R^{12}$)C(O)$OR^{12}$, —N($R^{12}$)C(O)N$(R^{12})_2$, —N($R^{12}$)C(═N$R^{12}$)N$(R^{12})_2$, or $C_1$-$C_6$alkyl, wherein each $R^{12}$ is hydrogen or $C_1$-$C_6$alkyl.

Such methods and uses further contemplate the use of a subgenera of embodiment (2) in which the substituents are selected as any and all combinations of structural formula (II), A, $R^1$-$R^4$, and $R^5$ as defined herein, including without limitation, the following:

Structural Formula II is one of formulae (Ia)-(Ih), and preferably is one of formulae (Id)-(Ih);

wherein A is selected from one of the following groups (aaaa)-(cccc):

(aaaa) A is —N═.

(bbbb) A is —N($R^A$)═, wherein $R^A$ is $C_1$-$C_6$alkyl, and wherein the compound further comprises a pharmaceutically acceptable anion.

(cccc) A is —N($R^A$)═, and the pharmaceutically acceptable anion is a halide.

wherein $R^1$-$R^4$ are selected from one of the following groups (d)-(ss), as defined above;

wherein $R^5$ is selected from one of the following groups (tt)-(zzz), as defined above.

In some embodiments, the compounds shown in Table I are utilized.

In certain embodiments, the methods and uses are used to treat diseased cells, tissues, organs, or pathological conditions and/or disease states in an animal associated with HSV activity and/or expression (e.g., a mammalian patient including, but not limited to, humans and veterinary animals). In this regard, various diseases and pathologies are amenable to treatment or prophylaxis using the present methods and compositions. A non-limiting exemplary list of these diseases and conditions includes, but is not limited to, oral infection (e.g., herpes) (e.g., oral ulcers), a genital infection (e.g., genital herpes), a neonatal infection, an ocular infection, and a central nervous system disorder (e.g., meningitis, encephalitis). In some embodiments, the disease or condition is characterized with unstable G-quadruplex activity including but not limited to viral conditions (e.g., HSV viral conditions).

Some embodiments of the present invention provide methods for administering an effective amount of a compound of the invention and at least one additional therapeutic agent (including, but not limited to, antivirals).

In a particular embodiment, the additional therapeutic agent(s) is an antiviral agent. Examples of antiviral agents include, but are not limited to, nucleoside inhibitors such as penciclovir, acyclovir, valacyclovir, and famciclovir; reverse transcriptase inhibitors such as azidothymidine (AZT), 2',3'-dideoxyinosine (DDI), 2',3'-didexoycytidine (DDC), didehydrothymidine (d4T), 2'-deoxy-3'-thiacytidine (3TC), abacavir succinate, and tenofovir disoproxil fumarate, nevirapine, delavirdine and efavirenz; protease inhibitors such as saquinavir, saquinavir mesylate, ritonavir, lopinavir, indinavir, nelfinavir mesylate, amprenavir, fosamprenavir, tipranavir, atazanavir, entry inhibitors such as maraviroc, vicriviroc, enfuvirtide, viral maturation inhibitors, agents targeting the expression of HIV genes, agents targeting key host cell genes and gene products involved in HIV replication, and other anti-HIV agents, iRNA agents, antisense RNA, vectors expressing iRNA agents or antisense RNA, PNA and antiviral antibodies.

Compositions within the scope of this invention include all compositions wherein the quindoline compounds having anti-HSV activity are contained in an amount which is effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for disorders responsive to induction of apoptosis. In one embodiment, about 0.01 to about 25 mg/kg is orally administered to treat, ameliorate, or prevent such disorders. For intramuscular injection, the dose is generally about one-half of the oral dose. For example, a suitable intramuscular dose would be about 0.0025 to about 25 mg/kg, or from about 0.01 to about 5 mg/kg.

The unit oral dose may comprise from about 0.01 to about 1000 mg, for example, about 0.1 to about 100 mg of the compound. The unit dose may be administered one or more times daily as one or more tablets or capsules each containing from about 0.1 to about 10 mg, conveniently about 0.25 to 50 mg of the compound or its solvates.

In a topical formulation, the compound may be present at a concentration of about 0.01 to 100 mg per gram of carrier. In a one embodiment, the compound is present at a concentration of about 0.07-1.0 mg/ml, for example, about 0.1-0.5 mg/ml, and in one embodiment, about 0.4 mg/ml.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. The preparations, particularly those preparations which can be administered orally or topically and which can be used for one type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by intravenous infusion, injection, topically or orally, contain from about 0.01 to 99 percent, in one embodiment from about 0.25 to 75 percent of active compound(s), together with the excipient.

The pharmaceutical compositions of the invention may be administered to any patient which may experience the beneficial effects of the compounds of the invention. Foremost among such patients are mammals, e.g., humans, although the invention is not intended to be so limited. Other patients include veterinary animals (cows, sheep, pigs, horses, dogs, cats and the like).

The compounds and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are in one embodiment dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The topical compositions of this invention are formulated in one embodiment as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The carriers may be those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762; each herein incorporated by reference in its entirety.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight. Lotions may be conveniently prepared by dissolving the active ingredient, in a suitable high molecular weight alcohol such as propylene glycol or polyethylene glycol.

One of ordinary skill in the art will readily recognize that the foregoing represents merely a detailed description of certain preferred embodiments of the present invention. Various modifications and alterations of the compositions and methods described above can readily be achieved using expertise available in the art and are within the scope of the invention.

Examples

The following examples are illustrative, but not limiting, of the compounds, compositions, and methods of the present invention. Other suitable modifications and adaptations of the variety of conditions and parameters normally encountered in clinical therapy and which are obvious to those skilled in the art are within the spirit and scope of the invention.

Example I

This example demonstrates that quindoline-derived compounds display significant anti-HSV activity.

Quindoline-derived compounds were first screened for their anti-herpetic activity. Increasing concentrations of compounds (from 25 to 400 nM) were added to U2OS cells infected with wild-type HSV-1 strain F at a MOI of 1. Supernatants were collected at 24 hours post infection (h.p.i.) and the reduction of viral particles production was determined by plaque reduction assay (PRA) (see, Artusi S., et al., Antiviral Res. 2015; 118:123-31; Callegaro S., et al., Sci. Rep. 2017; 7: 2341). Antiviral activities were determined as the concentration of compounds able to perform 50% inhibition of HSV-1 production (IC50). Cytotoxicity effects were evaluated in parallel by MTT assay and reported as the concentration of compounds able to kill 50% of the cells (CC50). The selectivity index (SI) was calculated as the ratio of CC50 to IC50. IC50, CC50 and SI values are reported in Table II.

TABLE II

Summary table of antiviral activities (IC50), cytotoxicities (CC50) and selectivity indexes (SI) of all the tested quindoline-derived compounds (compound titles as recited in Table I).

| | U2OS (Human osteosarcoma cell line) | | |
|---|---|---|---|
| Compound | $IC_{50}$ (nM) | $CC_{50}$ (nM) | SI |
| GSA-0932 | 132.3 | 14934.2 | 112.9 |
| GSA-0825 | 356.9 | 32709.2 | 91.64 |
| GSA-1512 | 255.6 | 18089.5 | 70.78 |
| GSA-1502 | 187.5 | 12881.9 | 68.70 |
| GSA-0903 | >200 | 6229.2 | <31.15 |
| GSA-1202 | 202.5 | 4315.3 | 21.31 |
| GSA-1504 | 225.3 | 4600.6 | 20.42 |
| Quintioline I | 155.9 | 2382.9 | 15.29 |
| GSA-0920 | >400 | 3620.6 | <9.05 |
| GSA-0820 | >400 | 2984.1 | <7.46 |
| GQC-05 | 310.6 | 1654.6 | 5.33 |

Almost all the compounds displayed IC50 values in the nanomolar range. Above all, GSA-0932 showed a pronounced antiviral activity (IC50=132.3 nM) together with low cytotoxicity (CC50=14934.2 nM), thus resulting in a promising selectivity index (SI=112.9) (FIG. 1). Consequently, GSA-0932 was been selected to be further characterized.

Example II

This example demonstrates that the lead compound GSA-0932 acts in early events of the viral life cycle.

Figure 2:
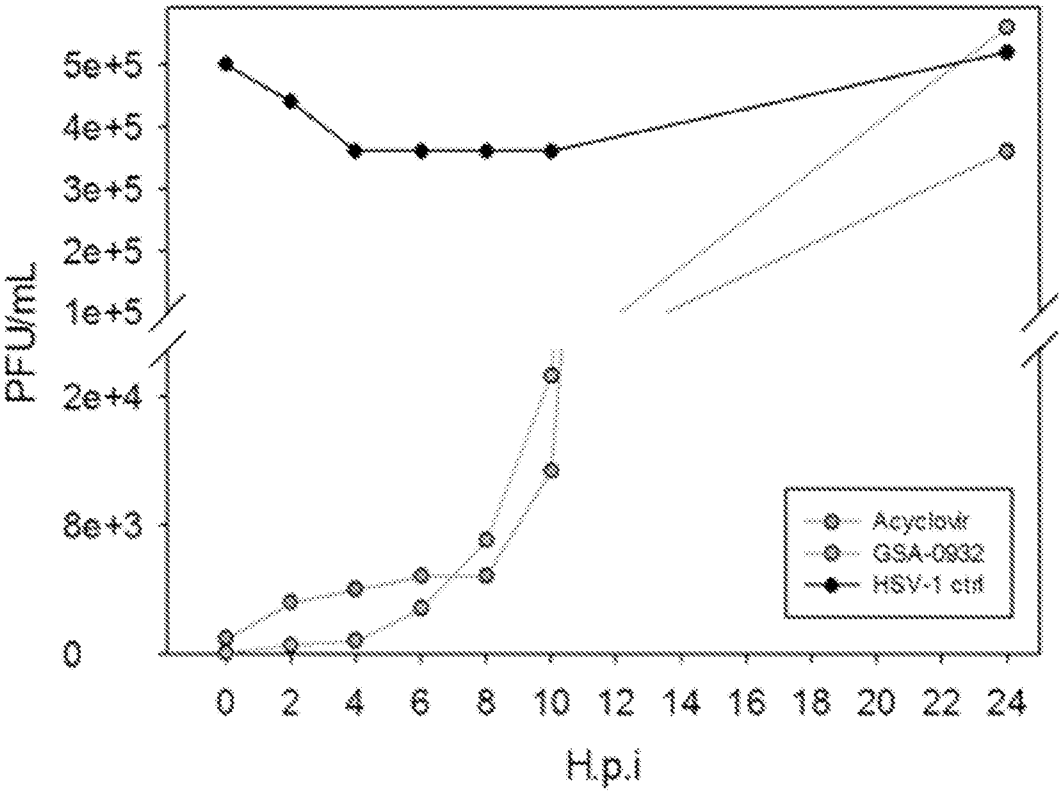
FIG. 2: TOA experiment with the test compound GSA-0932 (light blue lane and dots) and the reference drug Acyclovir (orange lane and dots). Data from infected cells treated in the same conditions but without the compounds are reported in black line and dots (HSV-1 control).

To assess the main and temporally last viral step targeted by the most promising compound, GSA-0932, a time of addition (TOA) assay was performed (see, FIG. 2) (see, Artusi S., et al., Antiviral Res. 2015; 118:123-31; Callegaro S., et al., Sci. Rep. 2017; 7: 2341; Daelemans D., et al., Nat.

Protoc. 2011; 6(6):925-33). This experiment permits determination of how long the addition of a compound can be postponed before it loses its antiviral activity. Since the HSV-1 replication cycle proceeds in a well-established chronological order, it is possible to investigate the last viral process targeted by a compound comparing its action to that of a reference drug in the time frame of replication events. The well characterized anti-HSV drug Acyclovir (ACV) was considered as reference (see, Artusi S., et al., Antiviral Res. 2015; 118:123-31; Callegaro S., et al., Sci. Rep. 2017; 7: 2341). HSV-1-infected U2OS cells were treated with a non-toxic concentration of GSA-0932 at different times post-infection (corresponding to different viral cycle steps): every 2 hours up to 10 h.p.i. Supernatants were collected at 30 h.p.i. and then titrated by PRA.

Treatment of HSV-1-infected U2OS cells with GSA-0932 kept infection controlled up to 6 h.p.i., whereas an exponential increase in the viral titer was reached from 8 to 10 h.p.i. From these results, it was assumed that GSA-0932 acts in early events of the viral life cycle. By overlapping TOA profile of ACV, a well known inhibitor of the viral replication (that occurs between 8-10 h.p.i.) (see, Elion G. B. J. Med. Virol. 1993; Suppl, 2-6), it was reasonable to hypothesize an inhibition of the replication machinery that causes a pronounced reduction in viral particles production.

Example III

This example demonstrates that GSA-0932 greatly stabilizes the HSV-1 G-quadruplex structures.

Circular dichroism (CD) was conducted to evaluate the binding and stabilizing activity of GSA-0932 to HSV-1 G-quadruplex structures (G4s). Three sequences were considered: two sequences forming a four-stacked-G-quartet structure (un2 and gp054a) and one forming a three-G-quartet G4 (un3) (see, Artusi S., et al., Antiviral Res. 2015; 118:123-31). HSV-1 G4s were analyzed at a final concentration of 4 μM in the presence of the physiological $K^+$ concentration (100 mM) or in the presence of lower $K^+$ concentration (2.5 mM) in order to better appreciate the effect of the compound in the case of extremely stable G4 structures (e.g. un2 sequence). Oligonucleotides were also analyzed in the absence or presence of 4-folds excess of GSA-0932. Melting temperatures measured by CD are reported in Table III.

TABLE III

Melting temperatures (Tm, ° C.) of HSV-1 un3, un2 and gp054a G-quadruplex folding sequences measured by CD spectroscopy in the absence or presence of 16 μM GSA-0932. ΔTm (° C.) indicates the variation in the oligonucleotide Tm in the presence of GSA-0932.

| | $K^+$ 2.5 mM | | $K^+$ 100 mM | |
|---|---|---|---|---|
| | Tm | ΔTm | Tm | ΔTm |
| un3 | 37.6 ± 0.4 | | 65.0 | |
| un3 + GSA-0932 | 56.4 ± 1.2 | 18.8 ± 0.8 | 66.4 | 1.4 |
| un2 | 82.4 ± 0.3 | | — | |
| un2 + GSA-0932 | >90 | >7.5 | — | — |
| gp054a | 58.9/>90 | | 57.4/82.4 | |
| gp054a + GSA-0932 | 74.5/>90 | 15.6 | 74.7/>90 | 17.4/>7.5 |

In 100 and 2.5 mM $K^+$, un3 sequence showed a stable parallel topology with a maximum peak at 260 nm and a negative peak at 240 nm. Un2 sequence, which displays a strong stability (above 90° C. at 100 mM $K^+$), was directly analyzed at 2.5 mM $K^+$ to better evaluate the effect of the compound. In this condition, the sequence displayed principally its well-known antiparallel conformation and a minor population with hybrid-mixed conformation (due to the lower stability of the sequence with low concentrations of $K^+$). In 100 mM $K^+$, gp054a showed a typical mixed-type conformation with two positive peaks at 290 and 260 nm. Addition of GSA-0932 induced an increase in the melting temperature of all the tested HSV-1 G-quadruplexes, proving its ability to effectively bind and greatly stabilize viral G-quadruplexes.

Figure 3:
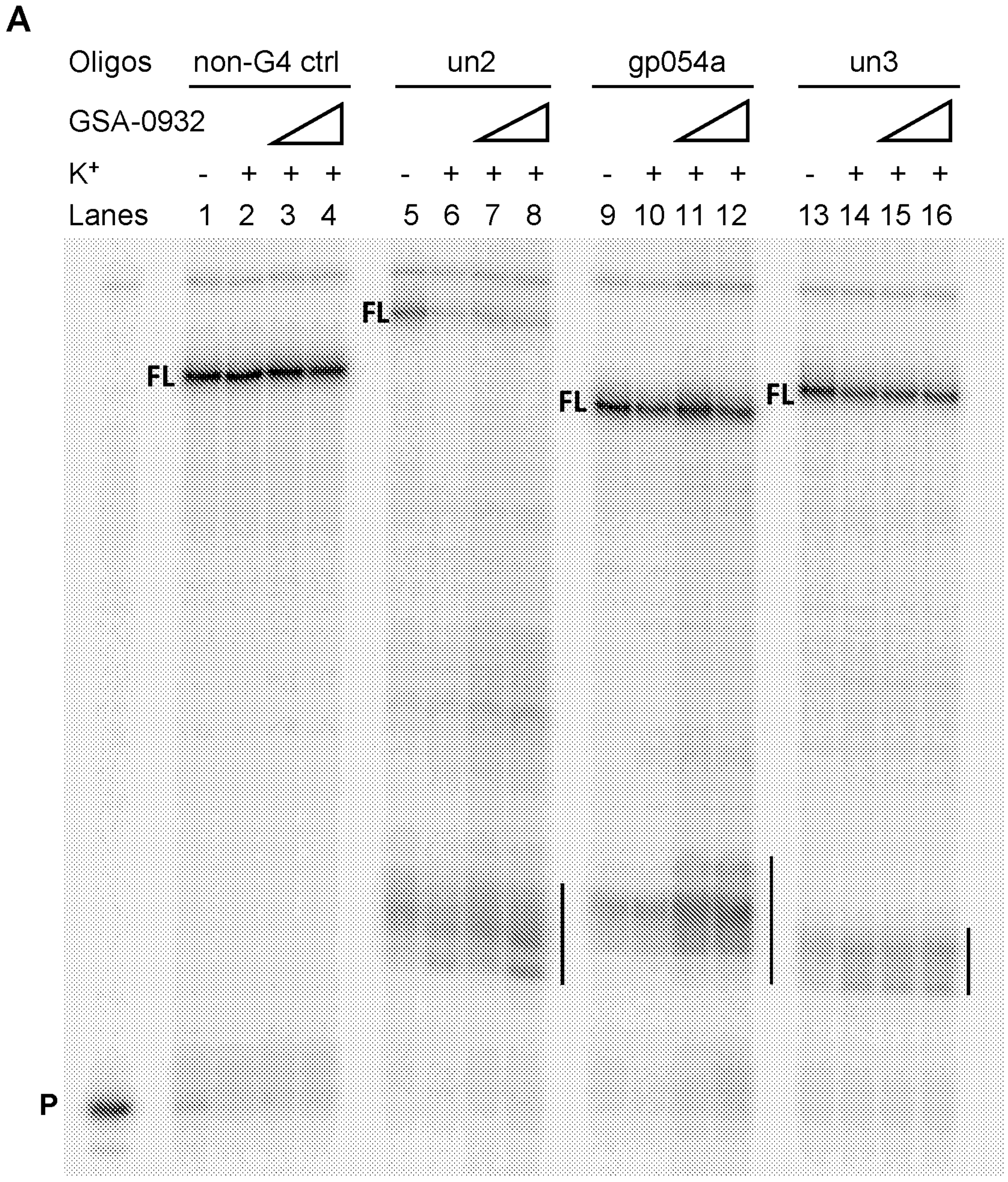
FIG. 3: Taq polymerase stop assay. A) Image of a typical Taq polymerase stop assay. The un2, un3, gp054a template were amplified by Taq polymerase in the absence (lanes 5-9-13) and in the presence of $K^+$, combined with increasing amounts (2-8 μM) of GSA-0932 (lanes 7-8, 11-12, 15-16) or same amount of DMSO as that in the ligand (lanes 6-10-14). Un3 was analyzed at 50 mM of $K^+$, while the other sequences were investigated at 0.5 mM of $K^+$. A template (non-G4 ctrl) unable to fold into G4 was also used as control (lanes 1-4). P stands for unreacted labeled primer, FL stands for full length product. G4-specific Taq polymerase stop sites are highlighted by vertical bars. B) Quantification of lanes 5-16 shown in FIG. 3. Quantification of stop bands corresponding to G4 and of the full length amplification product (FL) is shown.
Figure 3:
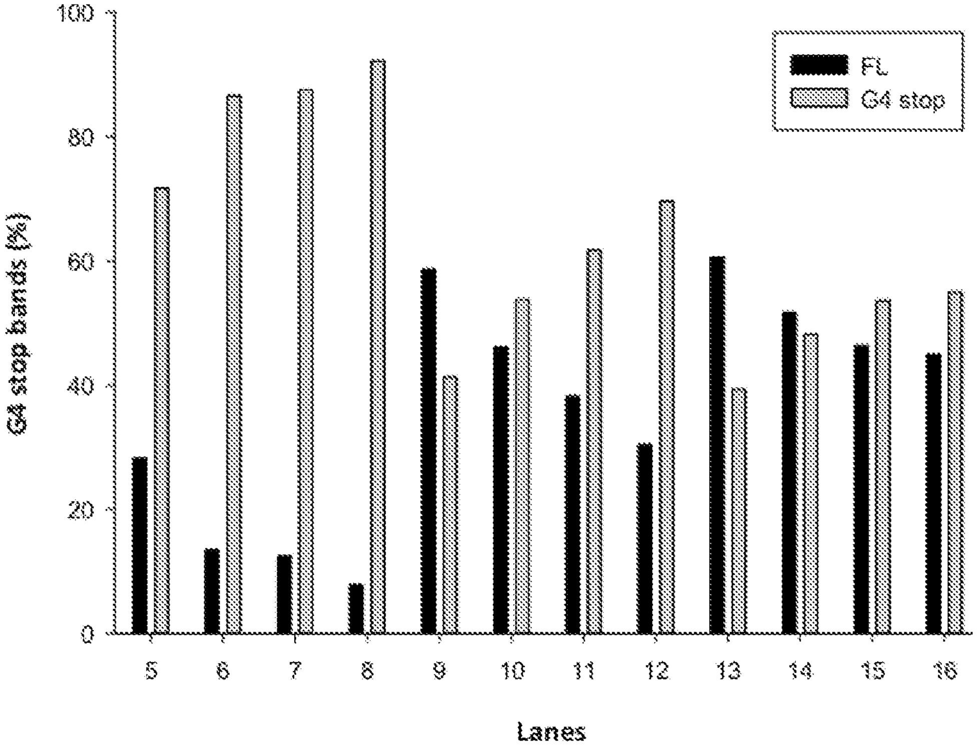

To confirm the increased stability of the viral G-quadruplexes in the presence of GSA-0932, a Taq polymerase stop assay was next set up (FIG. 3). Extended un2, un3 and gp054a forming sequences were used, containing additional flanking bases at the 3'-end: a primer annealing sequence and a 5-T linker region to separate the annealing sequence from the first G of the G-tract.

In the absence of $K^+$ (FIG. 3, lanes 5-9-13), all three G-quadruplex-forming sequences, especially un2 (FIG. 3, lane 5), displayed a marked stop site corresponding to the first G of the most 3' G-tract, indicating stable G-quadruplex folding. In the presence of $K^+$ (FIG. 3, lanes 6-10-14) the G-quadruplex-stop site increased in all templates, indicating that $K^+$ stimulates G-quadruplex folding and thus inhibits of polymerase progression. Un3 was analyzed at 50 mM of $K^+$, while the FIG. 3 other sequences were investigated at 0.5 mM of $K^+$ due to their higher stability. Upon addition of increasing amounts (2-8 μM) of GSA-0932, the intensity of the stop bands increased in a concentration dependent manner in all templates (FIG. 3A, lanes 5-9-13), along with reduction of the full-length amplicons, thus corroborating the effective stabilization of the G-quadruplexes by the compound. Quantification of the G-quadruplex-stop sites and full length products is reported in FIG. 3B. In contrast, the compound had no effect on a control DNA template unable to fold into G-quadruplex, indicating that the observed polymerase inhibition was G-quadruplex-dependent.

Example IV

This example demonstrates that GSA-0932 binds G-quadruplexes with a preference for the HSV-1 G-quadruplexes vs the telomeric sequence.

Competition electrospray ionization mass spectrometry (ESI-MS) experiments were performed in order to check the binding selectivity of GSA-0932 toward different G-quadruplex forming sequences (see, Callegaro S., et al., Sci. Rep. 2017; 7: 2341; Yuan G., et al., Mass Spectrom. Rev. 2011, 30, 1121-114210.1002/mas.20315). The viral un3, un2 and gp054a G4s were analyzed against the selected competitor hTel, the G-quadruplex-forming sequence of the human telomeric repeat, the most abundant cellular G-quadruplex. The oligonucleotides were diluted to final concentration of 4 μM and incubated with the compound at ratio DNA: compound 1:1.5 overnight at 4° C. Samples were analyzed by a Xevo G2-XS QT of mass spectrometer (Waters, Manchester, UK). Binding affinities were calculated for each experiment using the peak intensity for each species measured by MassLynx V4.1. Data are reported in Table IV.

TABLE IV

Relative binding affinity of GSA-0932 for un3, un2, gp054a and hTel G-quadruplex-folded oligonucleotides.

| Competing G4s | un3 | un2 | gp054a | Cell G4 (hTel) |
|---|---|---|---|---|
| un3/hTel | 50.3 ± 1.2 | | | 13.8 ± 0.2 |
| un2/hTel | | 38.9 ± 1.7 | | 11.1 ± 0.4 |
| gp054a/hTel | | | 57.3 ± 0.4 | — |

The viral un3, un2 and gp054a G-quadruplexes were preferentially bound by the compound over the telomeric G-quadruplex. This suggested a general selectivity of GSA-0932 toward HSV-1 G-quadruplexes.

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A method of treating a subject comprising a step of administering a therapeutically effective amount of a composition comprising a quindoline structure having significant anti-HSV activity to said subject, wherein the method of treating is for one or more of:

treating a Herpes Simplex Virus (HSV) infection in the subject;

suppressing a recurrent HSV infection in the subject;

treating a disease or condition characterized with unstable G-quadruplex activity, wherein the disease or condition characterized by unstable G-quadruplex activity is a HSV viral condition; and treatment of a viral disease characterized with unstable G-quadruplex activity, wherein the disease or condition characterized by unstable G-quadruplex activity is a viral condition, wherein the quindoline structure having significant anti-HSV activity is described by Formula I:

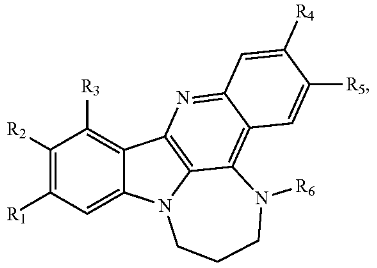

or a pharmaceutically salt, solvate and/or prodrug thereof;

wherein R1 is hydrogen or methyl;

wherein R2 is hydrogen,

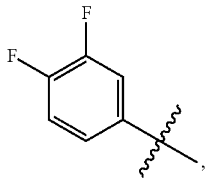,

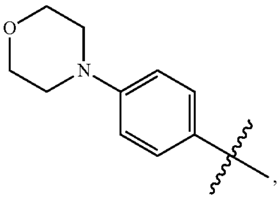,

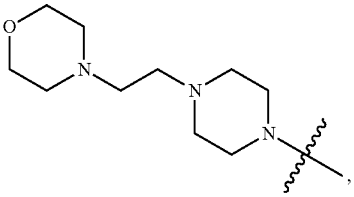,

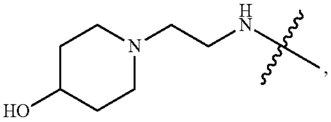, and

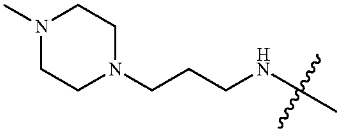.

wherein R3 is hydrogen or methyl;

wherein R4 is selected from hydrogen,

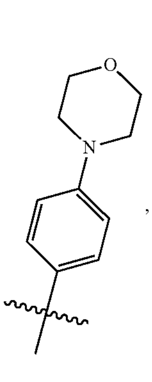,

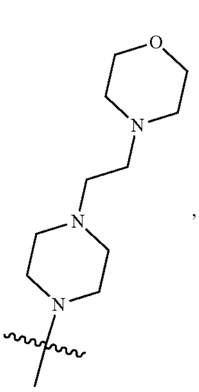,

-continued
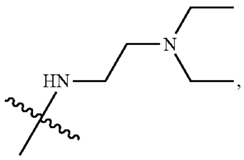,
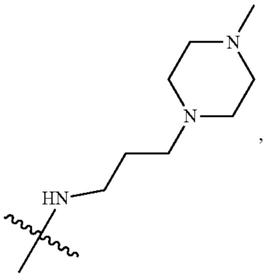,
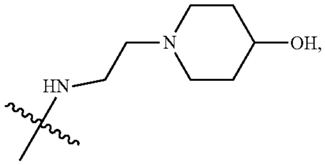
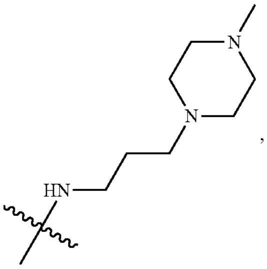,
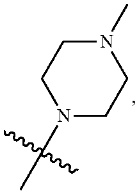,
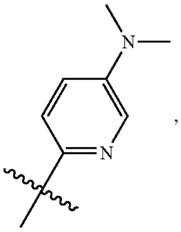,
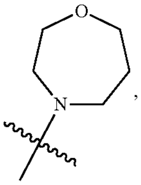,
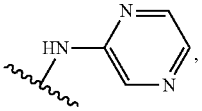
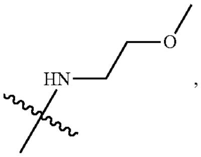,
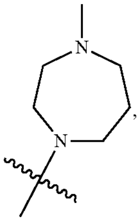
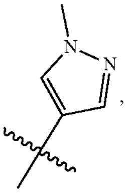
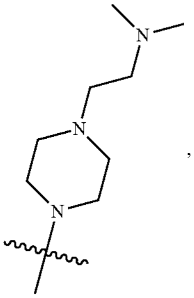,
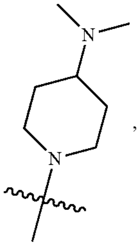,
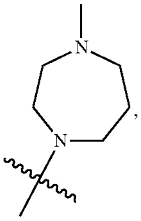
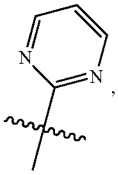
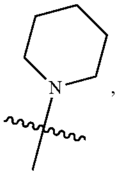, and
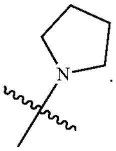
wherein R5 is selected from Hydrogen, halogen,
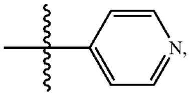
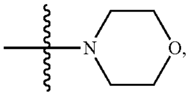
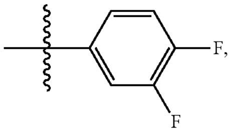
and
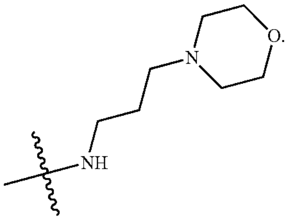
wherein R6 is selected from
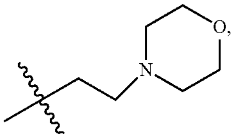
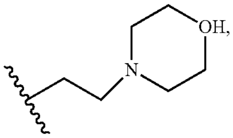
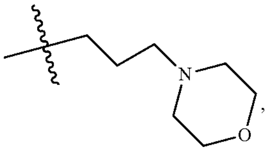
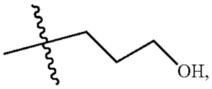
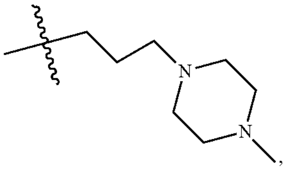
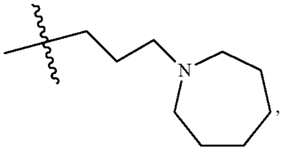
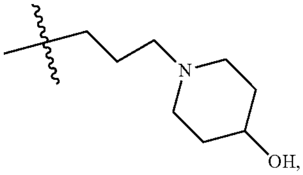
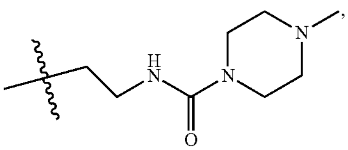
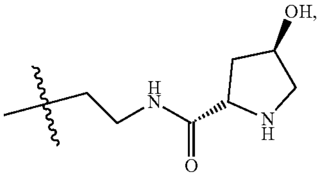

-continued

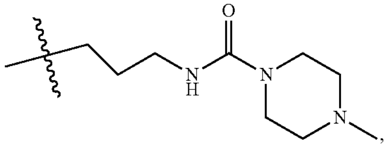

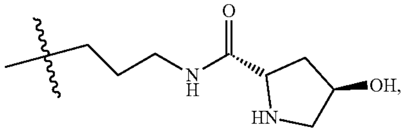

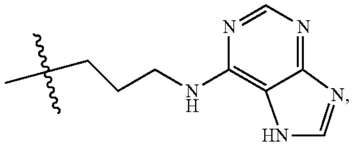

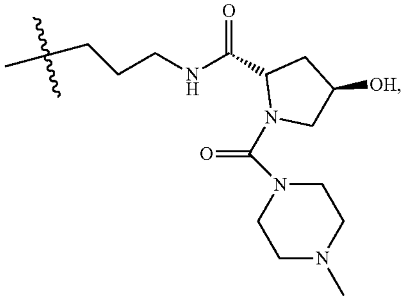

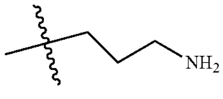

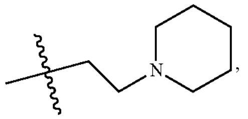

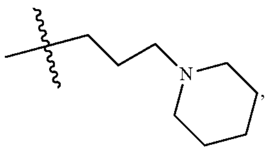

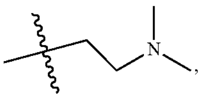

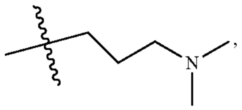

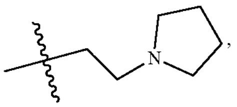

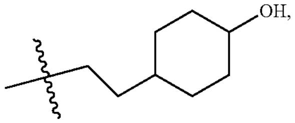

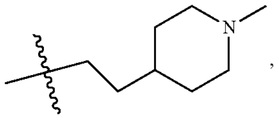

, and

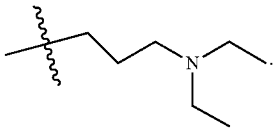

2. The method of claim 1, wherein said HSV infection is one or more of an oral infection, a genital infection, a neonatal infection, an ocular infection, and a central nervous system disorder.

3. The method of claim 1, wherein said HSV infection is a flare, recurrence, or HSV labialis following a primary HSV infection.

4. The method of claim 1, wherein said composition is administered intramuscularly, epidermally, subcutaneously, intravaginally, or via intra-respiratory mucosal injection.

5. The method of claim 1, wherein said treating said HSV infection comprises inducing rapid clearance of said HSV infection in said subject, and/or wherein said treating said HSV infection comprises reducing the severity of said HSV infection in said subject.

6. The method of claim 1, wherein said suppressing a recurrent HSV infection comprises preventing latent infection of HSV in said subject.

7. The method of claim 1, wherein administration of the composition results in stabilization of G-quadruplex (G4) formation.

8. The method of claim 1, wherein the subject is a human patient.

9. The method according to claim 1 wherein the viral disease characterized with unstable G-quadruplex activity is selected from Adenovirus infections, Herpes virus infections, Papillomavirus infections, Parvovirus infections, Polyomavirus infections, Poxvirus infections, Arbovirus infection, Arenavirus infections, Astrovirus infections, Birnavirus infections, Bunyavirus infections, Calicivirus infections, Coronavirus infections, Flavivirus infections, Hantavirus infections, Hepatitis A, Hepatitis B, Hepatitis C, and Hepatitis D, Mononegavirus infections, Filovirus infections, Paramyxovirus infections, and Rhabdovirus infections, Nidovirales Infections, Orthomyxoviridae infections, Picornavirus infections Enterovirus infections, Reovirus infections, Rotavirus infections, Retrovirus infections, lentivirus lentivirus infections, Togavirus infections, and Rubivirus infections.

10. The method according to claim 9 wherein the viral disease is an Adenovirus infection.

11. The method according to claim 9 wherein the viral disease is selected from a Herpes virus infection and a Picorna virus infection.

12. The method according to claim 11 wherein the herpes virus infection is caused by HSV-1, HSV-2 and/or varicella zoster virus.

13. The method of claim 1, wherein the compound is selected from the group consisting of:

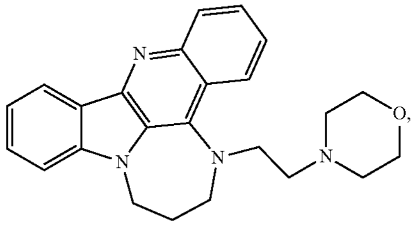

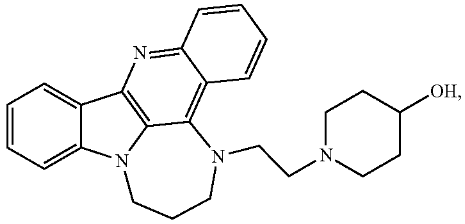

-continued
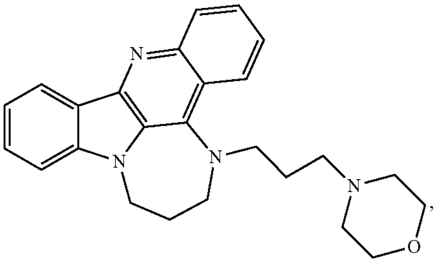
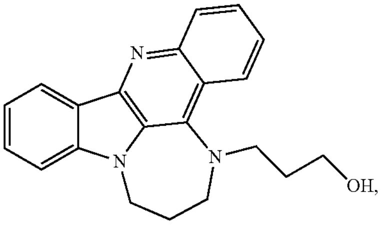
-continued
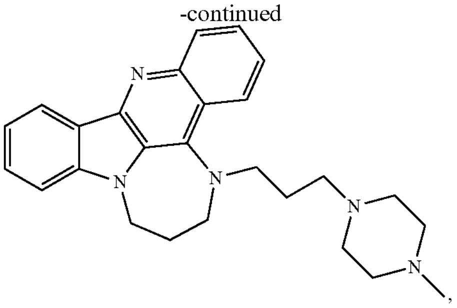
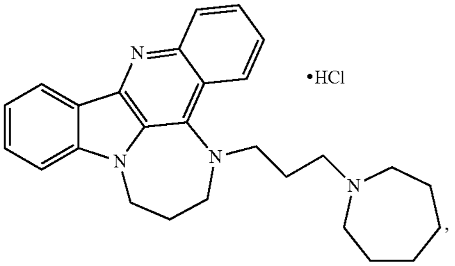
* * * * *